United States Patent
Greer et al.

(10) Patent No.: US 8,738,181 B2
(45) Date of Patent: May 27, 2014

(54) METHODS, DEVICES, AND SYSTEMS FOR AUTOMATED MOVEMENTS INVOLVING MEDICAL ROBOTS

(76) Inventors: Alexander Greer, Calgary (CA); Garnette Sutherland, Calgary (CA); Tim Fielding, Brampton (CA); Perry Newhook, Caledon (CA)

( * ) Notice: Subject to any disclaimer, the term of this patent is extended or adjusted under 35 U.S.C. 154(b) by 779 days.

(21) Appl. No.: 12/596,418

(22) PCT Filed: Apr. 16, 2008

(86) PCT No.: PCT/IB2008/003351
§ 371 (c)(1),
(2), (4) Date: Mar. 18, 2010

(87) PCT Pub. No.: WO2009/044287
PCT Pub. Date: Apr. 9, 2009

(65) Prior Publication Data
US 2010/0174410 A1    Jul. 8, 2010

Related U.S. Application Data

(60) Provisional application No. 60/912,142, filed on Apr. 16, 2007.

(51) Int. Cl.
*G01C 17/38*    (2006.01)
*G06F 19/00*    (2006.01)
(52) U.S. Cl.
USPC ........... 700/264; 700/245; 700/250; 600/407; 600/414; 600/417; 600/424; 600/130; 901/2; 901/14; 901/15; 702/95

(58) Field of Classification Search
USPC .......... 700/245, 264, 251, 250, 246; 600/429, 600/102, 407, 414, 417, 424, 130; 606/130, 606/1, 205; 395/99; 433/24, 213; 901/2, 14, 901/15; 702/95
See application file for complete search history.

(56) References Cited

U.S. PATENT DOCUMENTS

| | | | |
|---|---|---|---|
| 5,542,180 A | 8/1996 | Karani | 30/134 |
| 5,815,640 A | 9/1998 | Wang et al. | 395/86 |
| 6,606,539 B2 * | 8/2003 | Raab | 700/245 |
| 6,659,939 B2 * | 12/2003 | Moll et al. | 600/102 |

(Continued)

FOREIGN PATENT DOCUMENTS

| | | |
|---|---|---|
| EP | 1 698 438 | 9/2006 |
| GB | 2 119 965 | 11/1983 |

(Continued)

OTHER PUBLICATIONS

International Preliminary Report on Patentability issued in International Application No. PCT/IB2008/003351, dated Dec. 17, 2009.

(Continued)

*Primary Examiner* — Ronnie Mancho
(74) *Attorney, Agent, or Firm* — Fulbright & Jaworski LLP

(57) ABSTRACT

Methods, devices (such as computer readable media), and systems (such as computer systems) for defining and executing automated movements using robotic arms (such as robotic arms configured for use in performing surgical procedures), so that a remotely-located surgeon is relieved from causing the robotic arm to perform the automated movement through movement of an input device such as a hand controller.

25 Claims, 18 Drawing Sheets

(56) References Cited

U.S. PATENT DOCUMENTS

| | | |
|---|---|---|
| 6,837,883 B2 * | 1/2005 | Moll et al. ............ 606/1 |
| 6,949,106 B2 * | 9/2005 | Brock et al. ............ 606/130 |
| 7,087,049 B2 * | 8/2006 | Nowlin et al. ............ 606/1 |
| 7,155,316 B2 | 12/2006 | Sutherland et al. ............ 700/248 |
| 2003/0109857 A1 | 6/2003 | Sanchez et al. ............ 606/1 |

FOREIGN PATENT DOCUMENTS

| | | |
|---|---|---|
| JP | 60 095606 | 5/1985 |
| WO | WO 97/11416 | 3/1997 |
| WO | WO 00/60521 | 10/2000 |
| WO | WO 01/97694 | 12/2001 |
| WO | WO 03/077101 | 9/2003 |
| WO | WO 2006/033637 | 3/2006 |
| WO | WO 2006/052375 | 5/2006 |

OTHER PUBLICATIONS

International Search Report issued in International Application No. PCT/IB2008/003351, dated May 25, 2009.

Written Opinion issued in International Application No. PCT/IB2008/003351, dated May 25, 2009.

Troccaz, et al., "A passive arm with dynamic constraints: a solution to safety problems in medical robotics", *Proceedings of the International Conference on Systems, Man and Cybernetics*, 17: 166-171, 1993. XP010132245.

* cited by examiner

METHODS, DEVICES, AND SYSTEMS FOR AUTOMATED MOVEMENTS INVOLVING MEDICAL ROBOTS

CROSS REFERENCE TO RELATED APPLICATIONS

This application is a national phase application under 35 U.S.C. §371 of International Application No. PCT/IB2008/003351, filed Apr. 16, 2008, which claims priority to U.S. Provisional Patent Application Ser. No. 60/912,142, filed Apr. 16, 2007, the entire contents of each of which are incorporated by reference.

BACKGROUND

The present methods, devices, and systems relate generally to the field of surgical robotics, and more particularly to creating and executing one or more automated robotic arm movements to, for example, move a robotic arm along a path toward or away from a location where a tool or instrument (such as a surgical tool) held by the robotic arm can be exchanged or where a tool can be inserted for the first time. An example of a surgical robot that can be used in a procedure to which the present methods, devices, and systems relate is disclosed in U.S. Pat. No. 7,155,316 (the "'316 patent"), which is incorporated by reference.

SUMMARY

In a broad respect, the present techniques relate to programming, prior to an operation, a path along which a robotic arm can travel during a medical procedure. That programmed path may be referred to in this disclosure as an automated robotic arm movement, an automated movement, or auto-move for short, and such movements can involve movement by one, some, or all of the joints of a given robotic arm, including the base joint (e.g., the shoulder joint). While the path can be for any purpose, in some embodiments the path may be one that begins at a safe distance from an operational site and that ends at a location where a surgical tool (which may also be characterized as a medical or surgical instrument) held by the robotic arm can be exchanged, such as by a nurse. The path may be defined by two or more tool tip positions of the robotic arm (such as tool tip positions in Cartesian coordinate space of a tool that is held by or integral with the robotic arm) and two or more orientations of a tool axis associated with the tool. A given robotic arm may be referred to as a manipulator. The definitions may occur as a result of instructions or commands received from an operator inputting them via a hand controller or any other suitable input device. Such a hand controller may be the master in a master-slave relationship with the robotic arm. However, the orientation of the hand controller can be independent of the orientation of the tool at issue. A surgeon that executes one of the present automated movements is relieved from having to perform that movement in real time using a hand controller.

Thus, some embodiments of the present devices may take the form of computer readable media comprising machine readable instructions for receiving a first dataset for a starting position of an automated robotic arm movement; and receiving a second dataset for a second position of the automated robotic arm movement; where the automated robotic arm movement will involve movement of a robotic arm that is configured for use in surgery. In some embodiments, the first dataset comprises data sufficient to enable the determination of (a) a position of a tip of a tool held by or integral with the robotic arm, the tool having a longitudinal axis, and (b) an orientation of the longitudinal axis of the tool. In some embodiments, the second dataset comprises data sufficient to enable the determination of (a) a second position of the tip of the tool, and (b) a second orientation of the longitudinal axis of the tool. A dataset can comprise data sufficient to enable the determination of (a) a position of a tip of a given tool, and (b) an orientation of the longitudinal axis of the tool even when other data that is stored and accessible to a computer system executing the instructions is used to make the determination. For example, the dataset may comprise data that includes joint angles of the robotic arm, and the computer system executing the instructions may be configured with access to other data (such as robotic arm link lengths) that allow it to perform forward kinematics to make the determination. Further, such an automated robotic arm movement may be performed using a different tool than the one used in the generation of the first and second datasets (such that the different tool travels through the tool tip positions and in the tool axis orientations that define the movement, regardless of whether the robotic arm holding or integral with that different tool is in the same orientation at each of the tool tip positions as originally defined) by the computer system that is executing the instructions finding an inverse kinematics solution to determine a suitable set of robotic joints angles. In some embodiments, the position of the tool that is determined may be a position of a portion of the tool other than the tool tip.

In some embodiments, after one or more automated robotic arm movements have been programmed and stored, one may be selected for use during a surgical procedure (the selection may occur prior to or during the procedure), and may then be initiated during the procedure. The initiation instruction may be inputted through any suitable means, such as a hand controller that is used to control the movement of the robotic arm, and the initiation of the movement may be conditioned on some portion of the robotic arm or a structure held by the robotic arm (e.g., in more specific embodiments, the tip of the surgical tool held by the robotic arm) being within a pre-defined region, such as within a given distance from the programmed starting point of the movement (e.g., with a region surrounding the starting point), greater than a specified distance from the starting point, or outside a boundary that does not intersect the starting point. Collectively, these conditions are examples of a "proximity condition." In some embodiments, the present devices and systems will also recognize an instruction or command to stop an automated movement that is in progress, and can receive one or more instructions or commands to begin the movement again. In some embodiments, after an automated movement has concluded, the present devices and systems will recognize a command to execute a reverse of that movement, such as to return a newly-exchanged tool from a destination location back to a start location to enable an operator (e.g., a surgeon) to continue with a medical procedure.

Some embodiments of the present techniques may be characterized as customizable, or fully customizable, by a user. This means that the present systems are configured to allow a user to create a customized automated movement, rather than having to select one that exists when the system is powered up and that cannot be user-modified.

The automated movements that may be programmed using the present devices and systems may result in movement by a given robotic arm sufficient to cause its tool (e.g., a tool it is holding or that is integral with it) to moving along a line (or path) that is not coincident with the longitudinal axis of the tool. For example, a given automated movement may be programmed to cause a robotic arm to move laterally toward a tool exchange nurse and away from a patient, while the tool is held by the robotic arm in a non-lateral orientation.

Some embodiments of the present computer systems can be configured to run a conflict check on a given automated movement to determine, for example, whether the automated movement will violate any pre-defined no-go zones, any joint or velocity limits of the robotic arm, or the like, and display a suitable indicator specifying any one or more such violations on a GUI for review by a user.

Any embodiment of any of the present methods, devices (e.g., computer readable media), and systems (e.g., computer systems) may consist of or consist essentially of—rather than comprise/include/contain/have—the described functions, steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

BRIEF DESCRIPTION OF THE DRAWINGS

The following drawings illustrate by way of example and not limitation. Identical reference numerals do not necessarily indicate an identical structure, system, or display. Rather, the same reference numeral may be used to indicate a similar feature or a feature with similar functionality. Every feature of each embodiment is not always labeled in every figure in which that embodiment appears, in order to keep the figures clear. The hand controllers, manipulators and tools shown in the figures are drawn to scale, meaning the sizes of the depicted elements are accurate relative to each other.

FIG. 12 shows the CSD GUI following a user's selection of the "Automove" button (via a screen touch). In this state, a user can select under the "Arm Select" box in the "Mode Controls" tab the arm that the user wishes to define an automated movement for.

DESCRIPTION OF ILLUSTRATIVE EMBODIMENTS

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a method, device, or system that "comprises," "has," "contains," or "includes" one or more recited steps or elements possesses those recited steps or elements, but is not limited to possessing only those steps or elements; it may possess (i.e., cover) elements or steps that are not recited. Likewise, an element of a method, device, or system that "comprises," "has," "contains," or "includes" one or more recited features possesses those features, but is not limited to possessing only those features; it may possess features that are not recited. Similarly, a computer readable medium "comprising" (or "encoded with") machine readable instructions for performing certain steps is a computer readable medium that has machine readable instructions for implementing at least the recited steps, but also covers media having machine readable instructions for implementing additional, unrecited steps. Further, a computer system that is configured to perform at least certain functions is not limited to performing only the recited functions, and may be configured in a way or ways that are not specified provided the system is configured to perform the recited functions.

The terms "a" and "an" are defined as one or more than one unless this disclosure explicitly requires otherwise. The term "another" is defined as at least a second or more. The terms "substantially" is defined as at least close to (and includes) a given value or state (preferably within 10% of, more preferably within 1% of, and most preferably within 0.1% of). It will be understood by those of ordinary skill in this art that a tool that travels to the locations defining a given automated movement, where each location traveled-to is substantially identical to the user-defined version of that location, has followed that automated movement.

Figure 1:
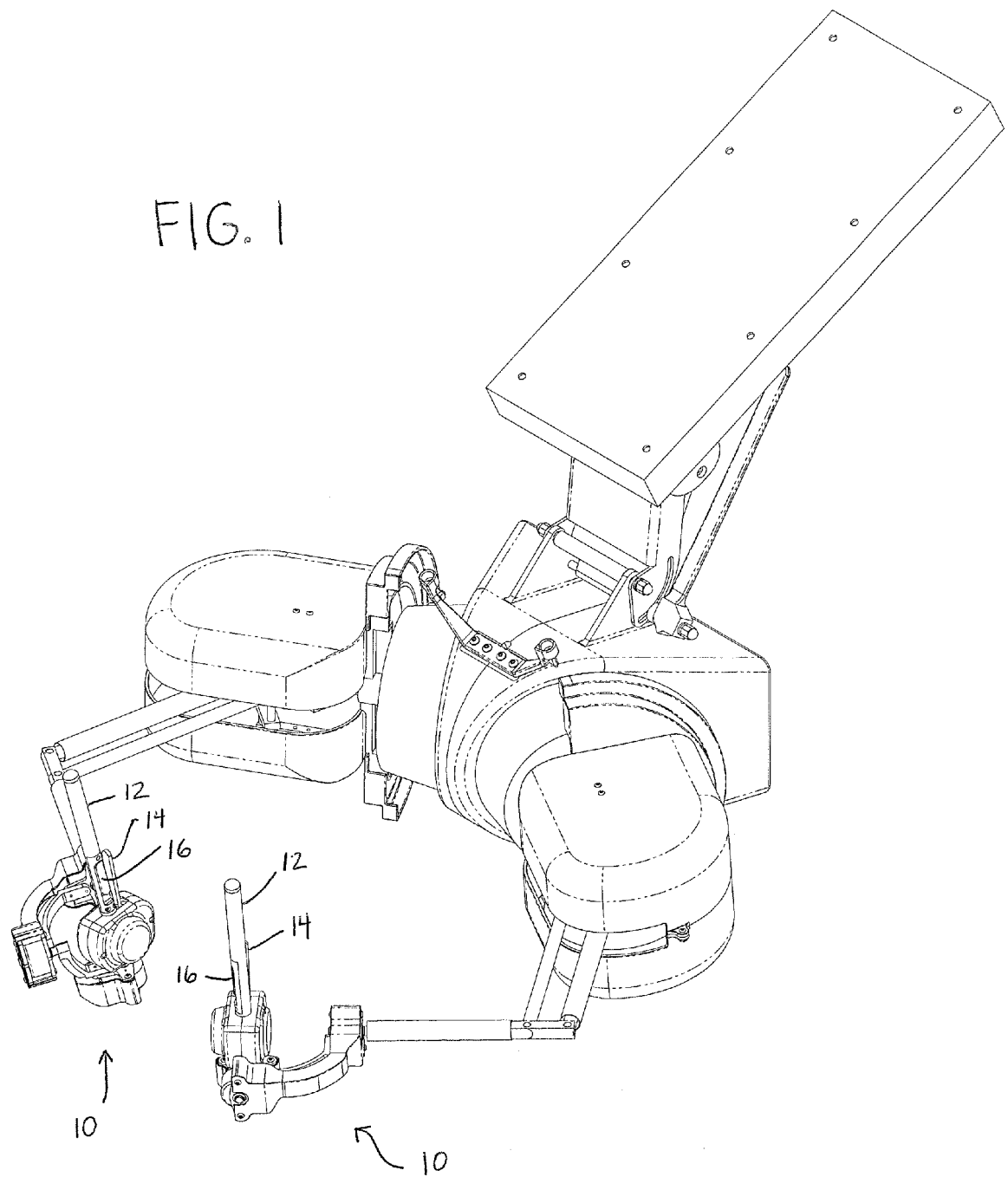
FIG. 1 is a perspective view of one embodiment of two input devices (hand controllers) that may be used consistent with the present techniques.

The apparatus to which the inventive techniques may be applied may, in some embodiments, include a slave robotic arm commanded by a master input device, such as a hand controller. An example of a pair of input devices (in the form of hand controllers) that can be used to control two different robotic arms, respectively, of a medical (e.g., surgical) robotic system are shown in FIG. 1. Input devices 10, which are mirror images of each other, each includes a stylus 12 that can be held like a long pen, lever 14 that can be squeezed toward stylus 12 to cause a tool integrated with or held by the slave robotic arm to actuate (e.g., squeezing lever 14 can cause forceps to close), and an enable/disable button 16 that can be depressed in a variety of ways in order to send a variety of commands to the present computer systems, including, for example, a short depression to send a command to activate or deactivate the link between the input device and a virtual manipulator shown on a given GUI and/or an actual manipulator (depending on whether the computer system is in simulation mode), and a depression and hold for a short time (e.g., a few seconds) to send a command to execute a given automated movement that has been associated with the manipulator to which that input device is linked. One way to hold a given input device 10 is to grasp stylus 12 so that lever 14 can be squeezed with the forefinger and so that button 16 can be touched with the thumb.

Figure 2:
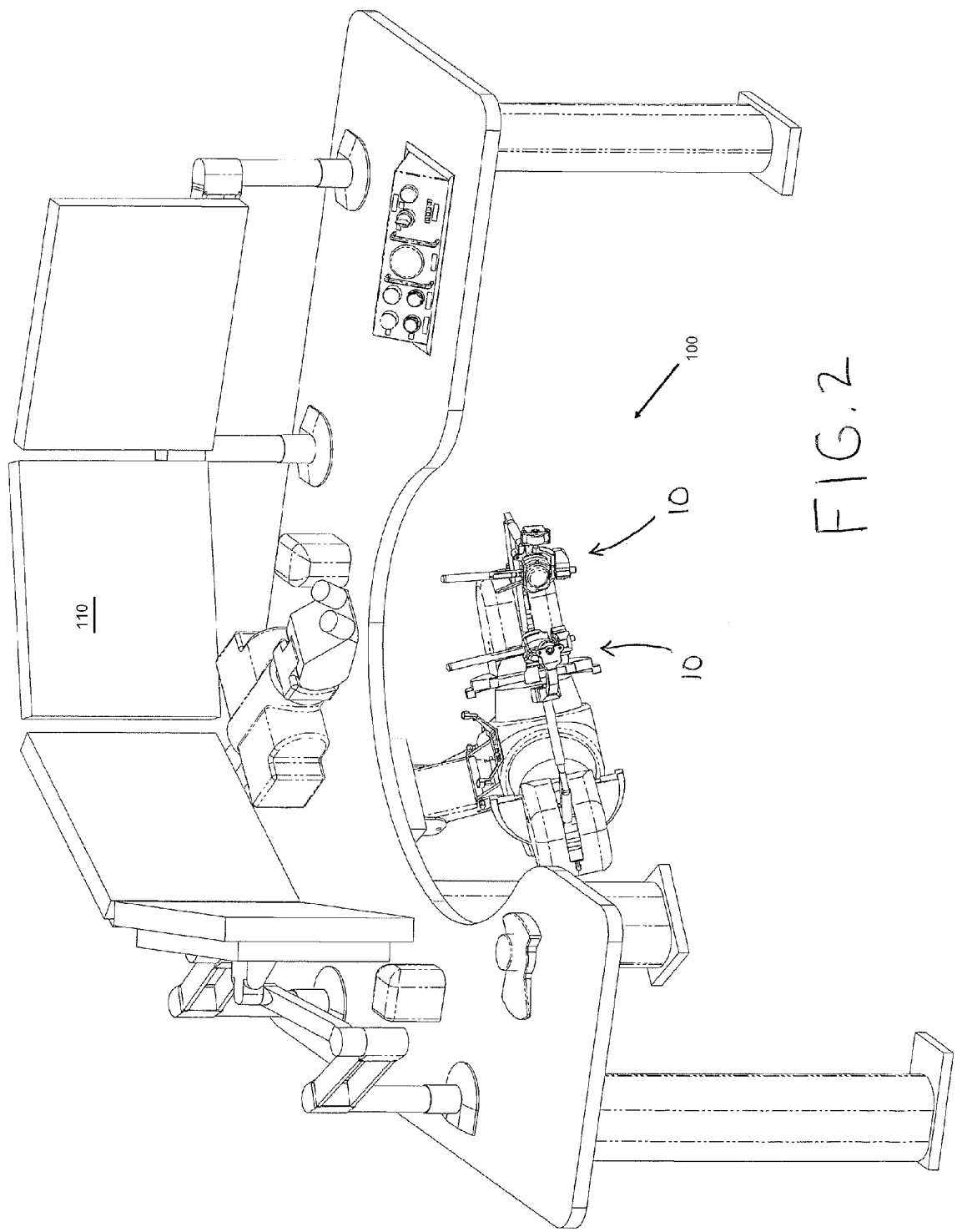
FIG. 2 is a perspective view of a workstation that can be used in planning automated movements.

FIG. 2 illustrates a perspective view of a workstation 100 that can be used in setting up automated movements for use by the robotic arms shown in the figures. In certain embodiments, workstation 100 comprises input devices 10 shown in FIG. 1 to control movement of the robotics arm, both actual and virtual. Workstation 100 may include a table (as shown) to which the input devices are secured as well as a series of display screens, any one or more of which can provide a graphical user interface (GUI) that can be used in setting up an automated movement for a given robotic arm. In a preferred embodiment, one of the present systems (e.g., one of the present computer systems) can be configured to cause display screen 110 to display a GUI that may include one or more data entry elements (e.g., buttons, radio buttons, drop-down menus, tabs, slider bars, text entry fields, and the like) that allow a user to use any suitable input means (such as touching the screen, using a mouse, and/or using a keyboard, etc.) to perform any of a variety of functions, including to select elements in order to define and store one or more automated movements (e.g., by selecting two or more tool positions and orientations, such as a tool tip position and a tool axis orientation (see FIG. 12, which shows an example of a longitudinal axis of a tool, which is also the axis (in the preferred embodiment) of the tool holders of the end effector of the robotic arm that is holding the tool, such that tool axis orientation may be determined from the end effector position, which may be known from the joint values of the robotic arm), select a robotic arm and a tool to use in defining the movement, select a stored automated movement for execution by a selected robotic arm (this is one manner of associating a robotic arm with a given automated movement), edit a stored automated movement, and delete a stored automated movement. The present computer systems can be configured to perform other functions discussed throughout this disclosure.

Figure 3:
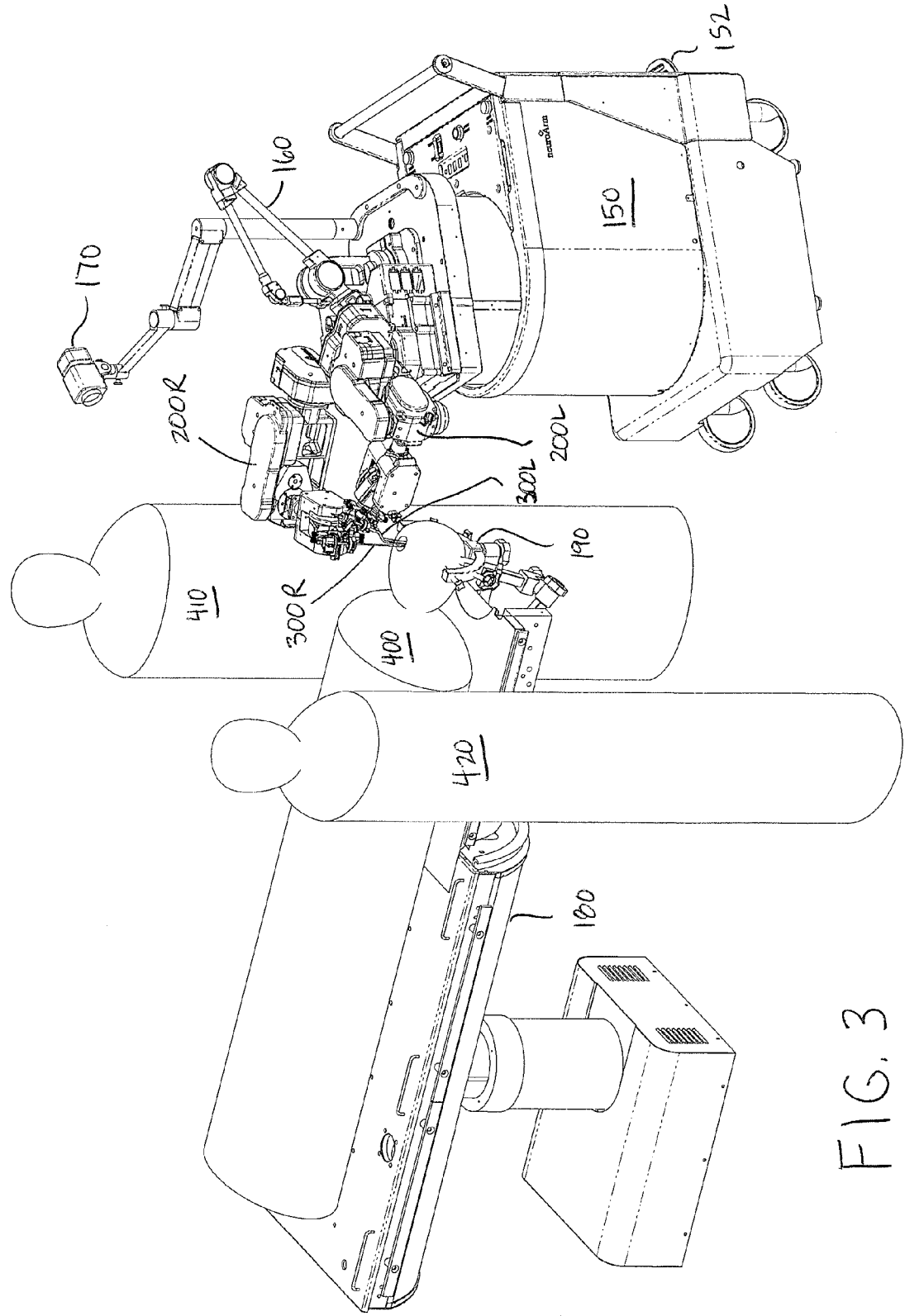
FIG. 3 is a perspective view of two robotic arms that are part of a remotely-controlled medical robotic system and that are in use in a medical (e.g., surgical) procedure. A schematic representation of a subject is shown positioned on an operating table, flanked by individuals on either side, who are also shown schematically. The person on the far side of the table represents a tool exchange nurse and the person on the near side of the table represents an assistant surgeon.
Figure 4:
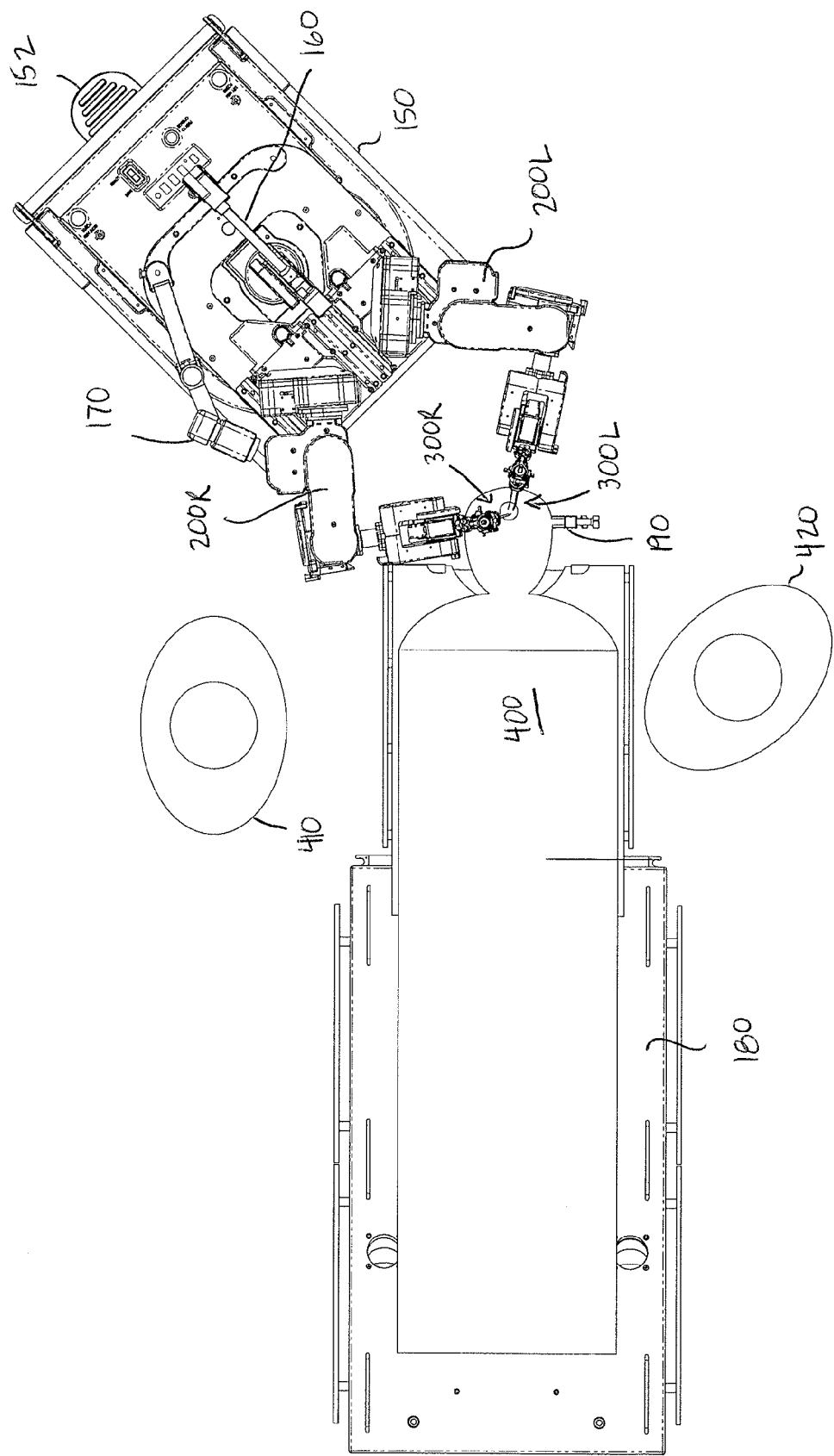
FIG. 4 is a top view of the arrangement shown in FIG. 3.

FIGS. 3-10 are provided to illustrate various aspects of automated movements that may be programmed according to the present techniques. In FIGS. 3 and 4, a medical (e.g., surgical, or more specifically microsurgical) procedure is shown being performed on a schematic representation 400 of a patient. A schematic representation of a tool exchange nurse 410 is shown positioned on one side of the patient, near the patient's head and the medical robotic system, and a schematic representation of an assisting surgeon 420 is shown positioned on the other side of the patient, near the patient's head and the medical robotic system. Left and right robotic arms 200L and 200R, respectively, are shown secured to a mobile base station 150 (having a foot lever 152 that renders it position-lockable) to which a digitizing arm 160 (for use in physical registration of one or both robotic arms to an image or images of a portion of the patient) and a field camera 170 (via an adjustable stand) are also secured. (The designations "left" and "right" are used only to more easily distinguish between the tools/instruments shown in the figures, which can each be used by either robotic arm.) Patient 400 is shown positioned on a patient support surface in the form of a top surface of an operating table 180, and the patient's head is secured using pins of a head clamp 190. Left robotic arm 200L is holding a tool (also characterizable as an instrument) 300L, which is depicted as a pair of forceps, and right robotic arm 200R is holding a tool 300R, which is depicted as a needle. In other embodiments, the tools may be integrated with the robotic arms. The tools are shown inserted in the patient's head through an opening that represents a burr hole or craniotomy entry hole.

Figure 5:
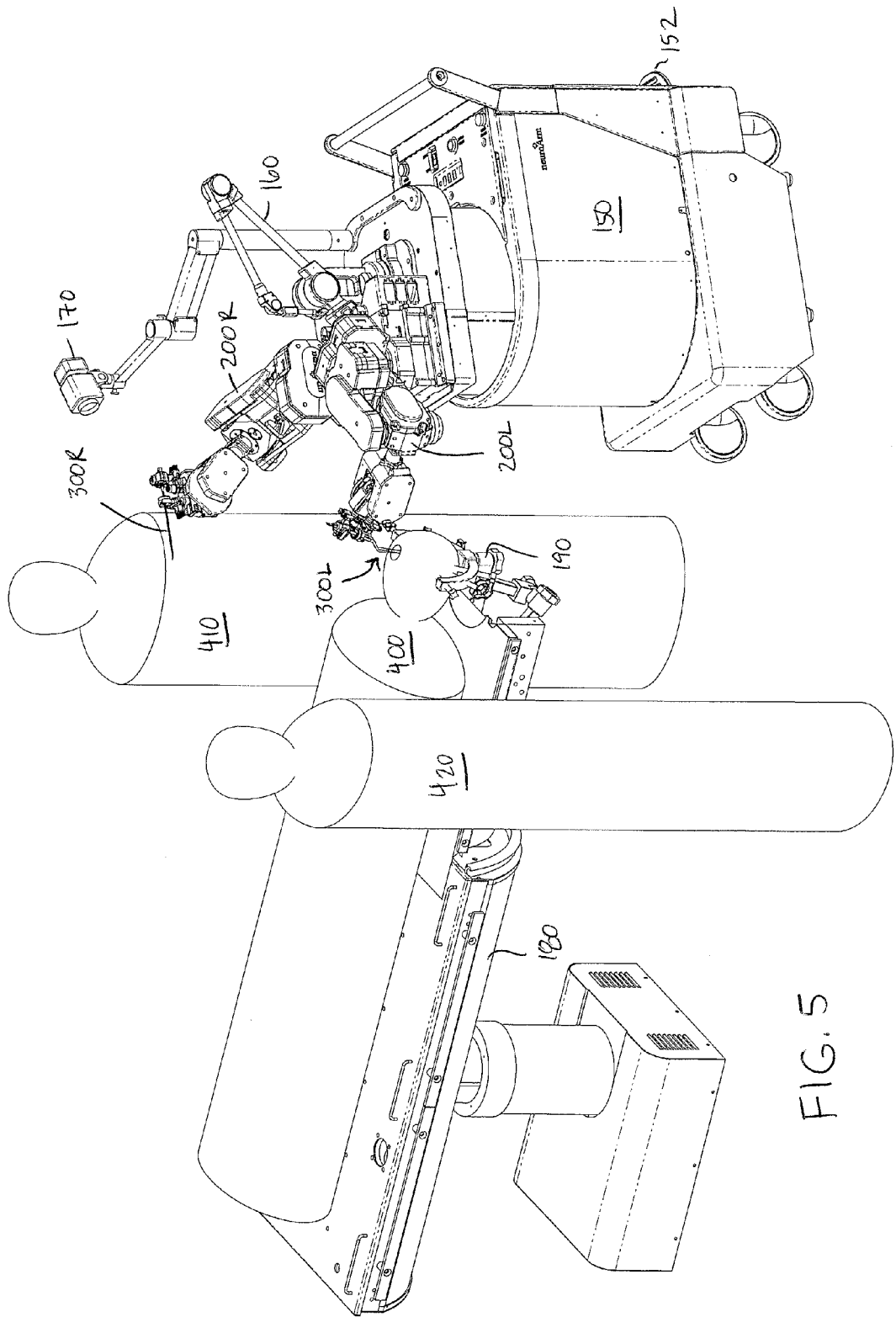
FIG. 5 is a perspective view of the arrangement shown in FIG. 3, in which the tool held by the right robotic arm is in a tool exchange position proximate the tool exchange nurse.
Figure 6:
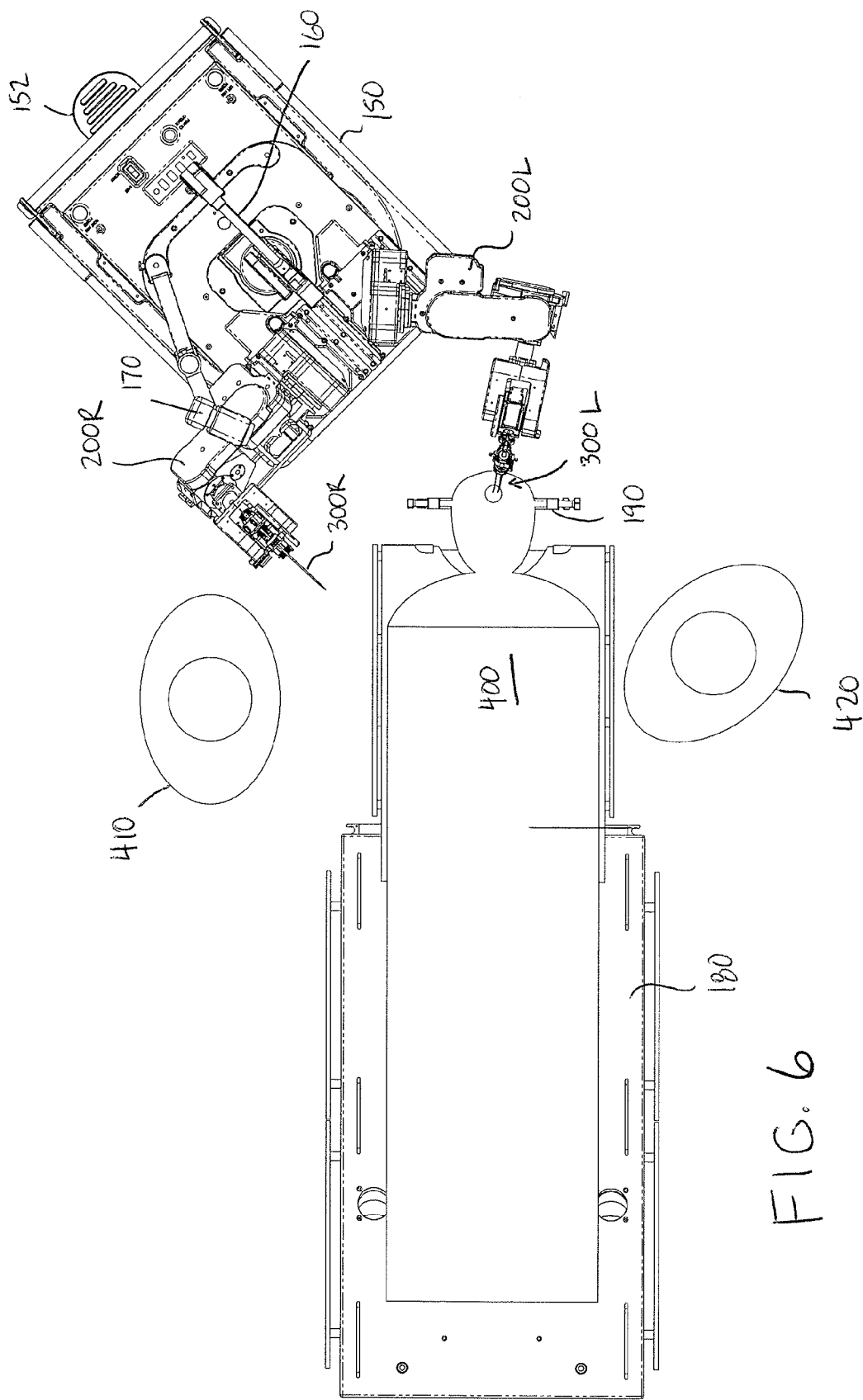
FIG. 6 is a top view of the arrangement shown in FIG. 5.

FIGS. 5 and 6 show right tool 300R located outside of the patient's head and in a tool exchange location, which can correspond to a destination point of an automated movement programmable according to embodiments of the present techniques. In this orientation, tool exchange nurse 410 may decouple right tool 300R from right robotic arm 200R, and replace it with another tool that the nurse couples to the robotic arm. Left tool 300L is shown remaining in place in the patient's head.

Figure 7:
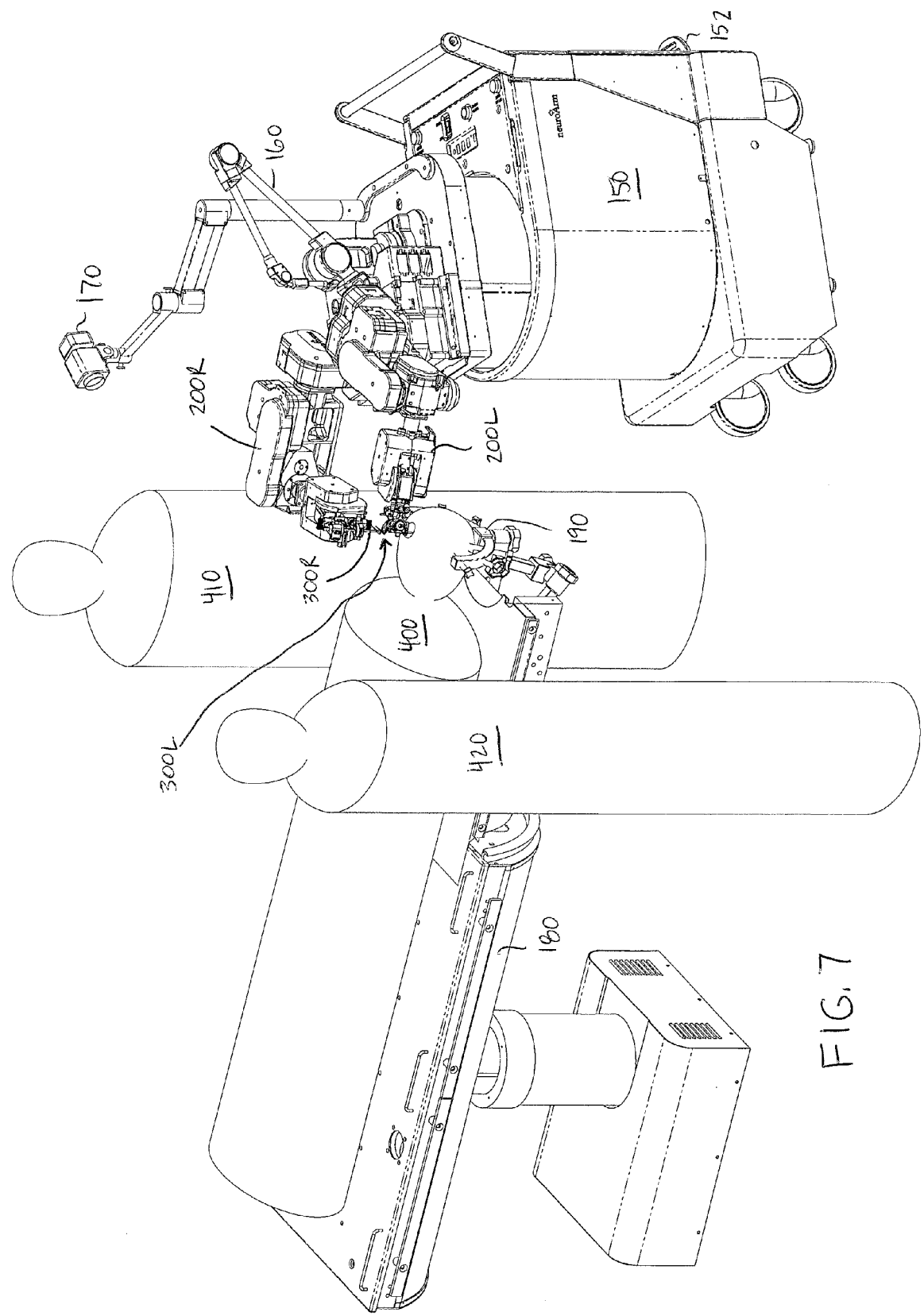
FIG. 7 is a perspective view of the arrangement shown in FIG. 3, in which the tool held by the left robotic arm (and, more generally, the left robotic arm itself) is in a "safe" position, outside of the subject's head, and in position to satisfy a proximity condition of the type discussed in the Summary.
Figure 8:
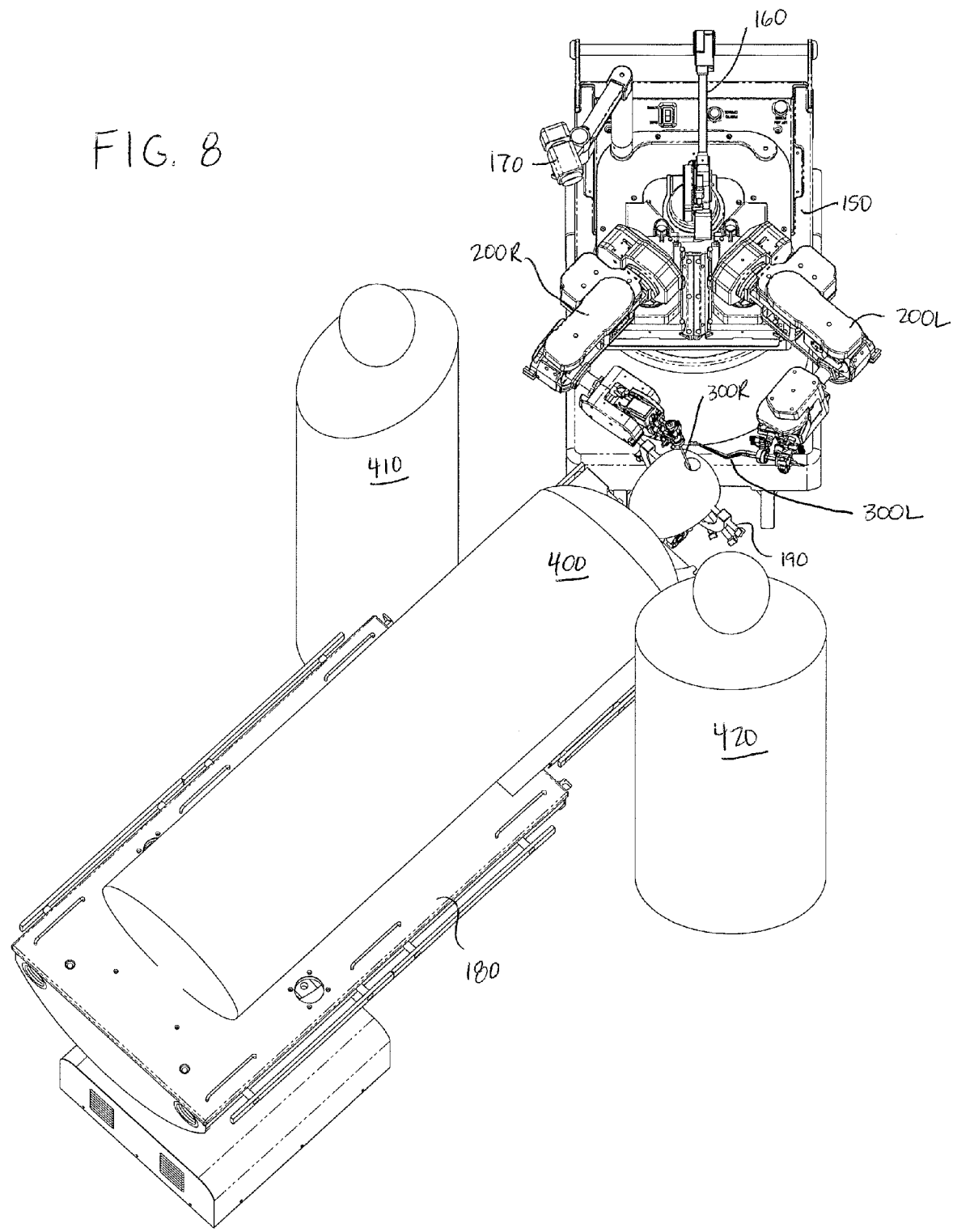
FIG. 8 is a top perspective view of the arrangement shown in FIG. 7.

FIGS. 7 and 8 show right tool 300R located in the patient's head, while left tool 300L is positioned in a safe location outside of the patient's head. This safe location may satisfy one of the present proximity conditions that may serve as a prerequisite to executing an automated movement. One example proximity condition is one in which the tool tip must be outside of the patient's head. A surgeon may move left tool 300L to the location shown in FIGS. 7 and 8 when he or she desires to start an automated movement, such as an automated movement that will cause left robotic arm 200L to move tool 300L into a tool exchange position. If the location of left tool 300L (and, more specifically, the tip of tool 300L) satisfy the applicable proximity condition(s) (e.g., is a safe distance outside patient 400's head), then the automated movement can proceed following the surgeon's depression and hold of button 16 on the relevant input device 10.

Figure 9:
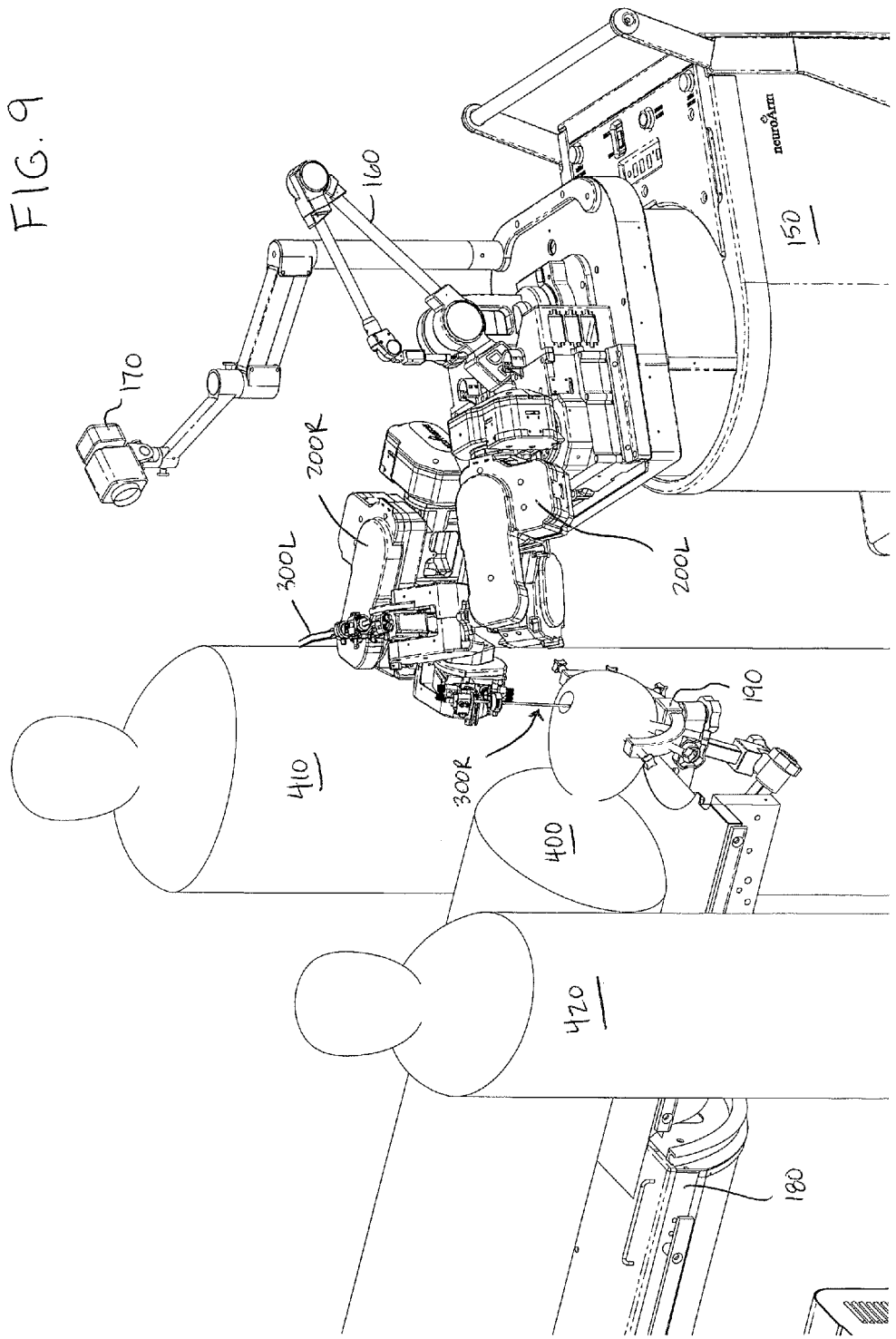
FIG. 9 is a perspective view of the arrangement shown in FIG. 7, in which the left robotic arm has been moved into a tool exchange position proximate the tool exchange nurse.
Figure 10:
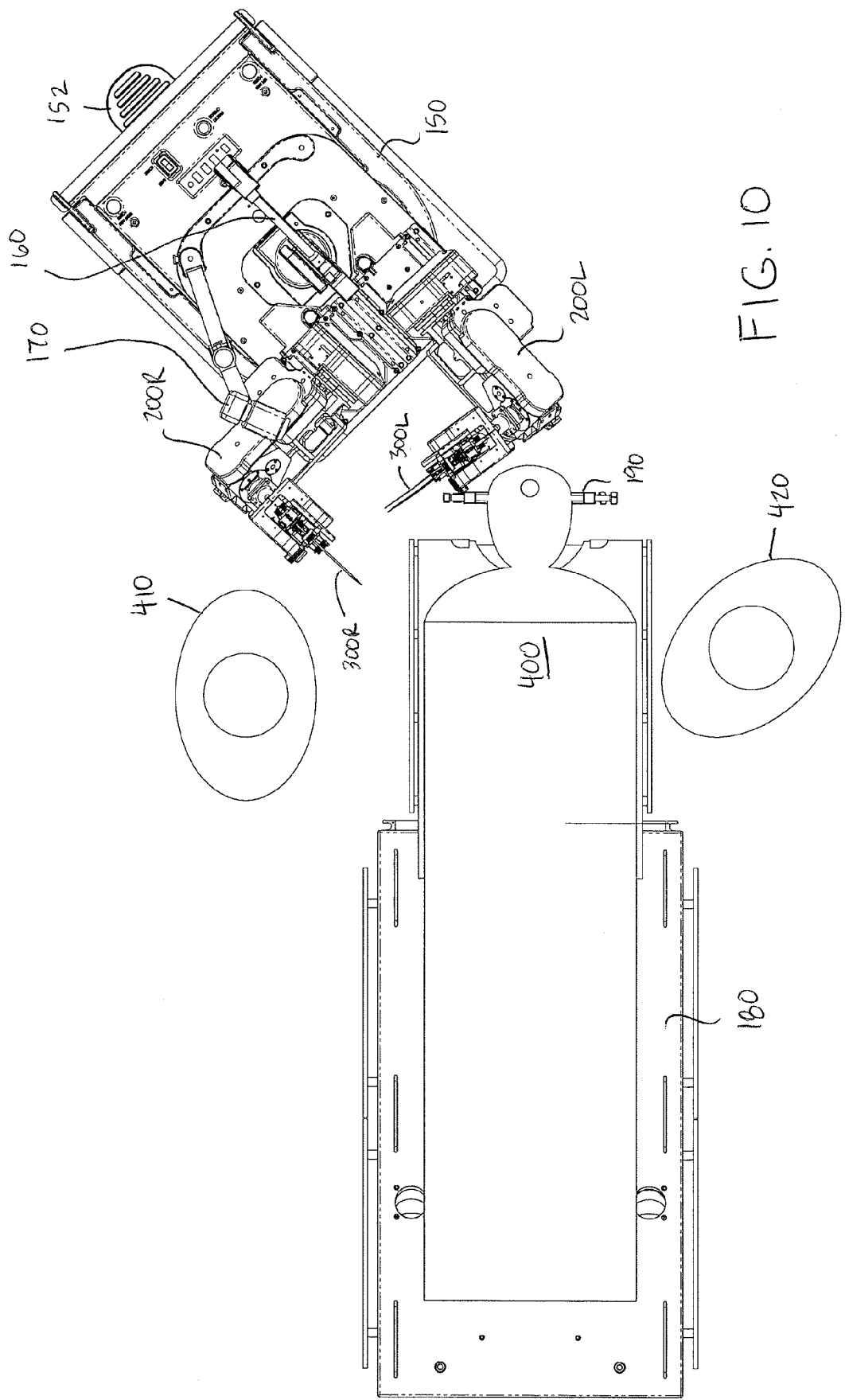
FIG. 10 is a top view in which both robotic arms shown in FIGS. 3-9 have been moved into tool exchange positions.

FIG. 9 shows the result of execution of the commanded automated movement because left tool 300L is in a tool exchange position (such as one that can be the destination point for a given automated movement). FIG. 10 shows the result of execution of two automated movements, where both the tools are in tool exchange locations that can correspond to destination points for the automated movements.

Automated Movements Generally

Some embodiments of the present automated movements may be used to move a manipulator from a microsurgical position, to a tool exchange position, and back again without requiring the operator to perform that motion using the relevant hand controller. Several automated movements can be pre-programmed and stored using embodiments of the present computer systems. Upon start up, the operator (e.g., a surgeon) would choose which of the preprogrammed moves he would like to have (e.g., as a tool exchange automated movement). The computer system may be configured to tie the selected automated movement to button 16 on the relevant hand controller to allow the operator to command the movement without going into the Automove GUI page (discussed and shown below), or having to take his hand off of the relevant hand controller.

The present automated movements comprise two or more taught (e.g., user-defined or user-selected) points. As a minimum, a given automated movement comprises a start and an end (e.g., termination) point. This will define a motion that is a straight line between the two points. If a non-linear motion is desired based, for example, on a desire to avoid a potential obstacle, one or more intermediate (e.g., waypoints) can also be defined. The resulting path will then involve movement through each of the waypoints in between the start and end points.

Automated Movement Creation

Certain embodiments of the present computer systems may be configured to perform some or all of the functions described below. Those of ordinary skill in the art having the benefit of this disclosure will be able to write code (machine readable instructions, which can be implemented through software, hardware, firmware, or a combination of any two or more of these) without undue experimentation for accomplishing the features and functions (including the graphical user interfaces) described below and shown in the figures.

Figure 11:
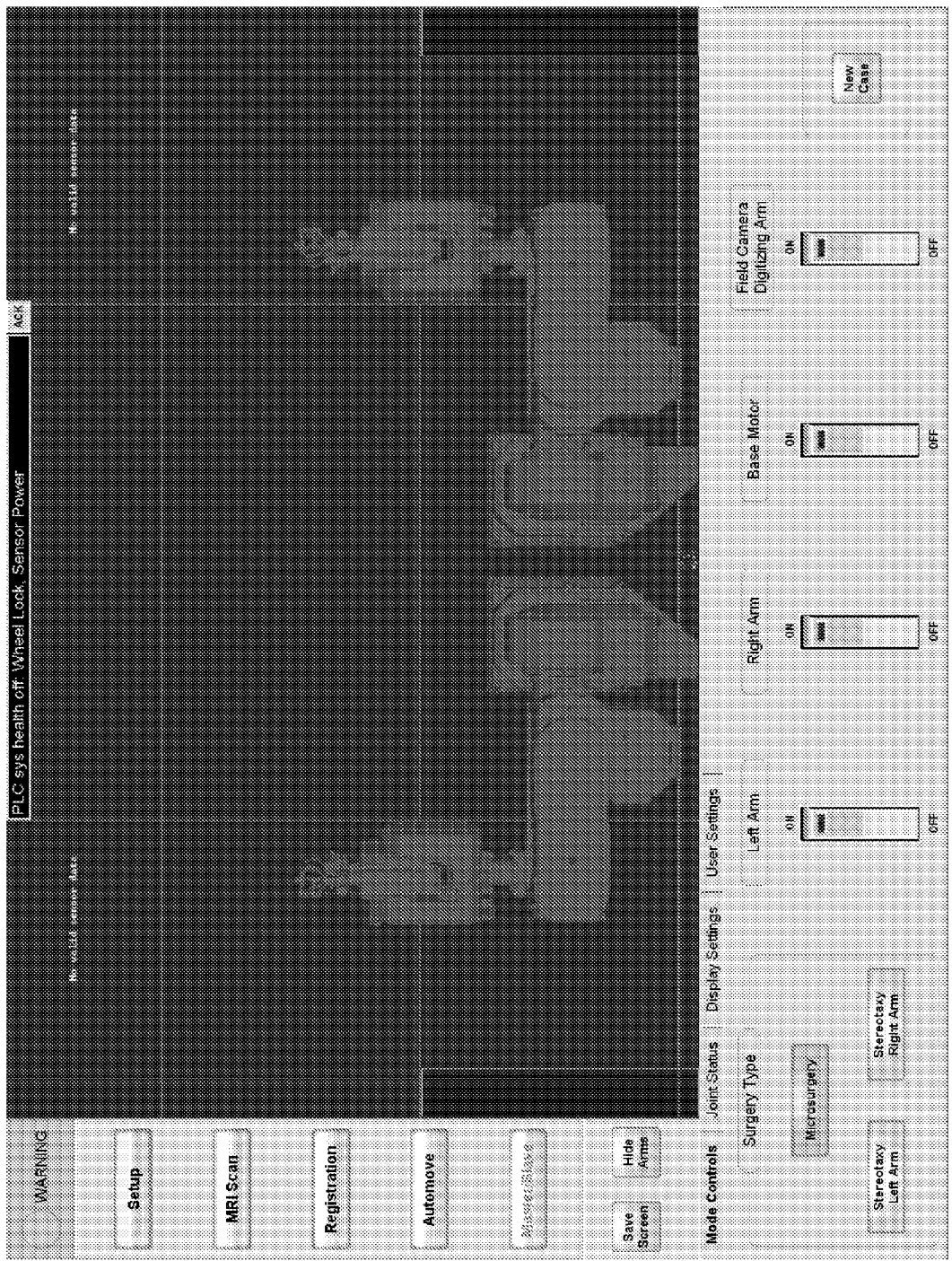
FIG. 11 shows a graphical user interface (GUI) that can be used to program automated movements. The GUI is in the Setup mode in this figure, and the "Surgery Type" under the "Mode Controls" tab has been selected to be "Microsurgery." This GUI may be referred to in this disclosure as a Command Status Display (CSD) GUI.
Figure 12:
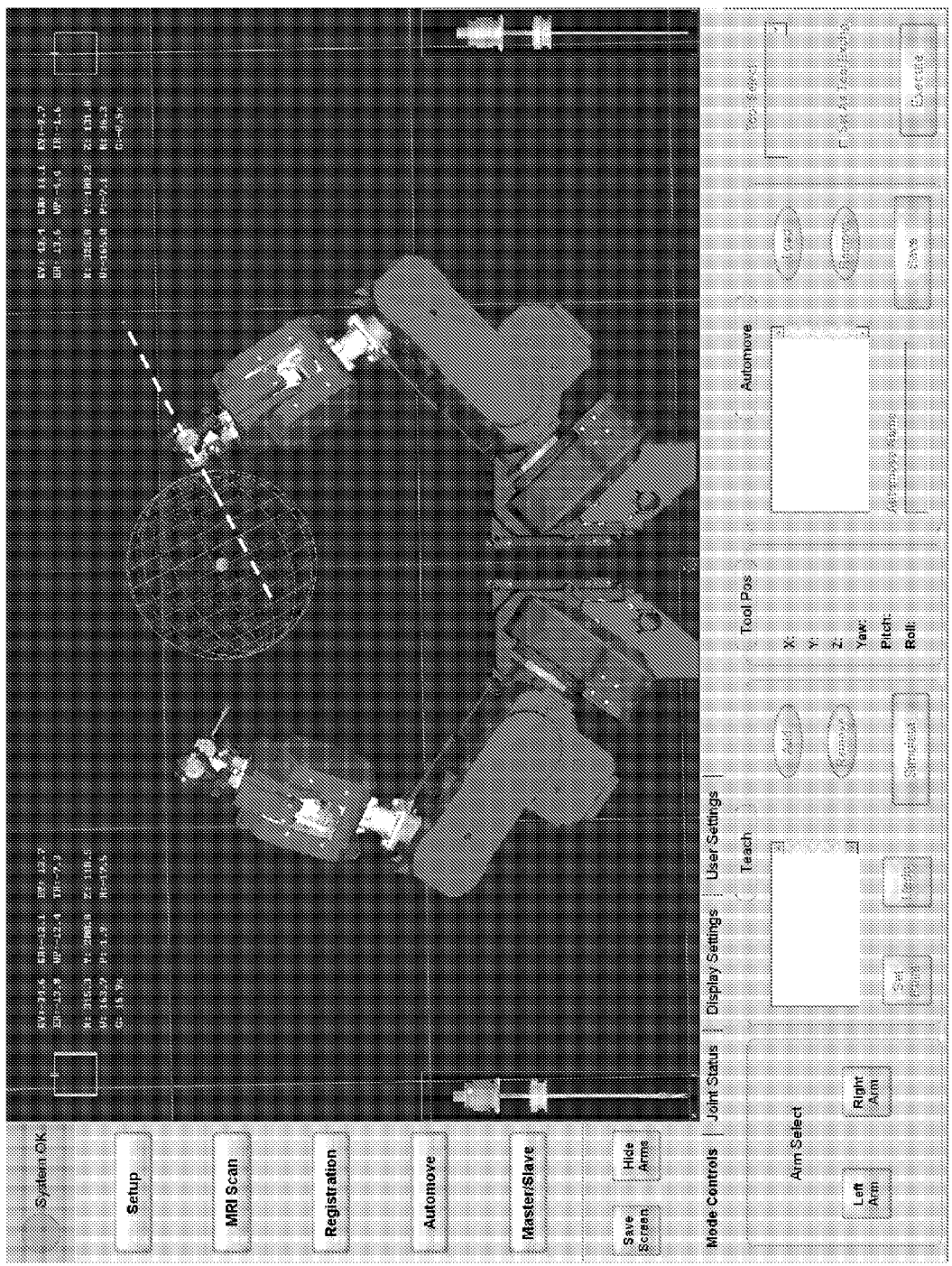
Figure 13:
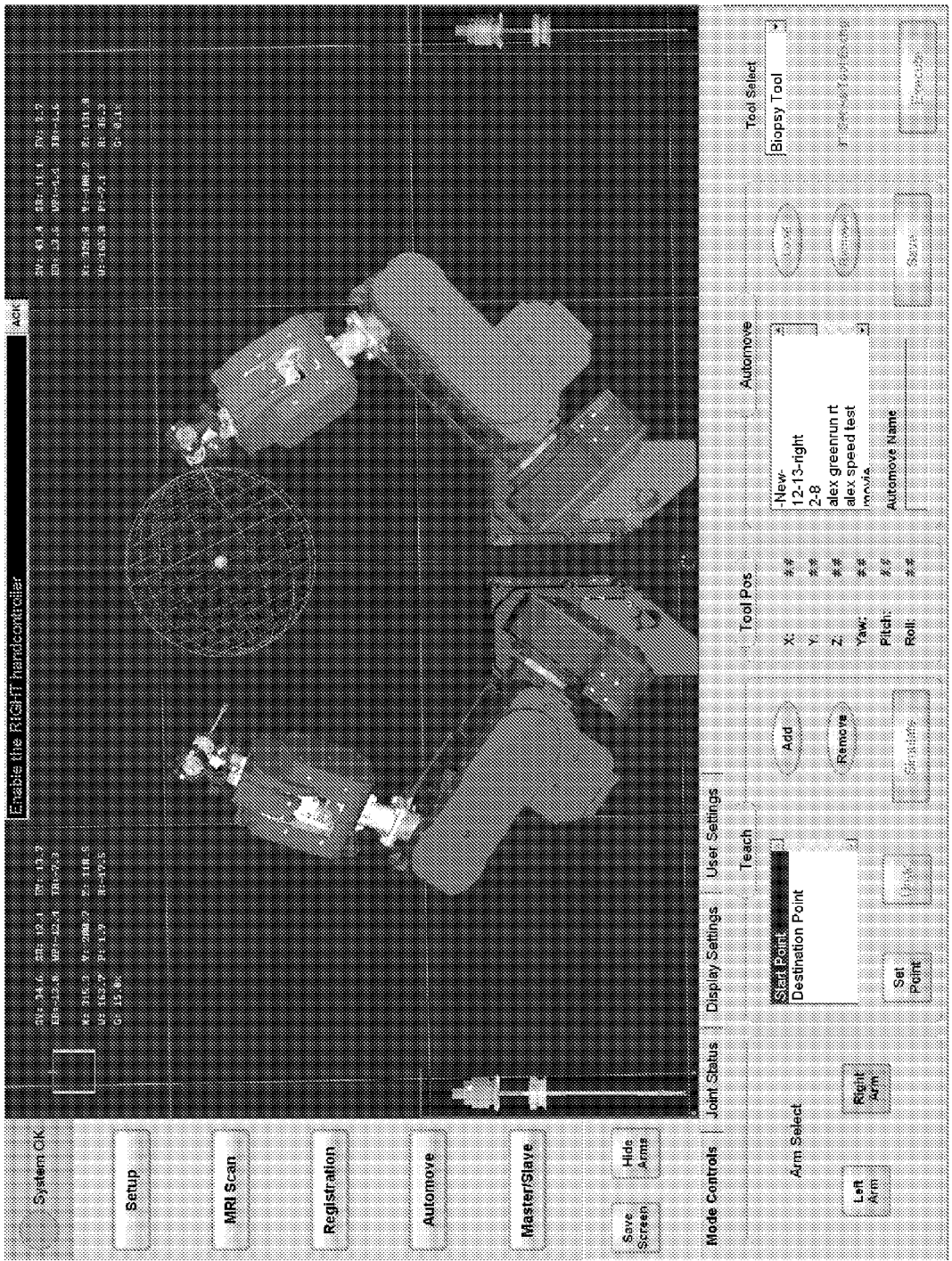
FIG. 13 shows the CSD GUI in the Automove state in which the Right Arm has been selected, and the user is given the option to select a tool for the right arm using the "Tool Select" drop-down menu under the "Mode Controls" tab.
Figure 14:
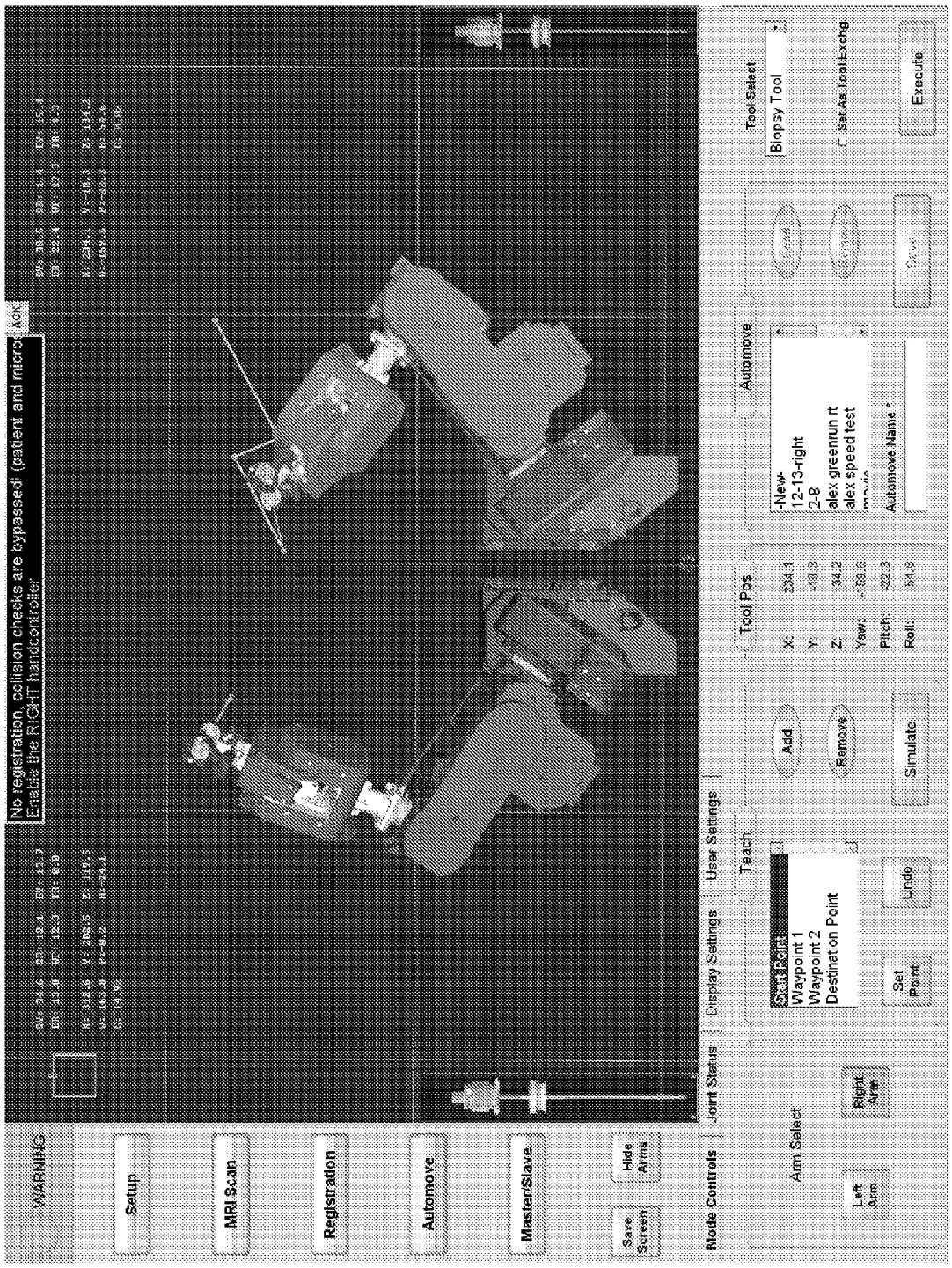
FIG. 14 shows the CSD GUI in the Automove state, and further shows that an automove comprising four points (Start Point, Waypoint 1, Waypoint 2, and Destination Point) have been selected and are shown connected on the screen.

Automated movements may be created in the "Automove" page on the CSD GUI, shown for example in FIG. 12. FIGS. 11-17 show examples of the states of the CSD GUI that can be displayed, for example, on display 110. The computer system can either be in simulation mode (see, e.g., FIG. 17), or fully configured for manipulator motion. Separate automated movements may be created for left and right robotic arms, such as those shown in FIGS. 3-10, which can be identical to or at least similar in construction, operation, and functionality to those disclosed in the '316 patent. The following sequence of steps may be followed, and the following functions performed, consistent with some embodiments of the present methods, devices, and systems (e.g., computer systems) to create, select, and execute an automated movement. A given automated movement may involve movement by one, some, or all of the joints of a given manipulator, including the base joint (e.g., the shoulder joint).

First, the computer system mode may be set to "Microsurgery" on the GUI "Setup" page under the "Surgery Type" box on the "Mode Controls" tab, as shown in FIG. 11. The computer system is configured, at this point, to show only grayed (unhighlighted) versions of the robotic arms on the GUI, indicating that neither has been powered on. The representations of the robotic arms on the screen are graphical (meaning they are not actual images of the arms), but the representations may be to scale, as they are in the present figures.

Next, a user may select the "Automove" button on the left side of the GUI. As a result, the GUI may display a screen similar to what is shown in FIG. 12, in which a graphical representation of a subject's (e.g., a patient's) head is shown (as a wire-frame sphere), with an indicator (e.g., a ball, which can be colored) as the center of the graphical head, along with the graphical representations of the robotic arms and the tools selected for each to give the user a view of their positions relative to the subject's head.

Under the "Arm Select" box under the "Mode Controls" tab, a user can select an arm ("Left Arm" or "Right Arm") the user wishes to define a given automated movement for (see FIG. 12). The computer system may be configured such that, if the arms are powered (because, e.g., the On/Off button (see FIG. 11) has been set to "On" for those arms), the display will show the current position of the manipulators. A user may select a tool under the "Tool Select" drop-down menu under the "Mode Controls" tab shown in FIG. 13 to associate a particular tool with a selected robotic arm.

Next, a user may send a command to the computer system (which may be characterized as receiving the command) that results from movement of a given hand controller causing virtual movement on the GUI of the graphical representation of the associated robotic arm by picking up the hand controller that corresponds to the selected robotic arm (e.g., right hand controller 10 for right robotic arm 200R), depressing the enable button (e.g., button 16, which may also be characterized as a stylus enable button), and moving the virtual manipulator via movement of the enabled hand controller to any desired location for a starting point of the desired automated movement. When desired location is reached, a user can send a command to the computer system to disengage the hand controller from the selected robotic arm such that any movement of that hand controller no longer causes virtual movement of the robotic arm (as reflected on the GUI) by depressing the same button (e.g., button 16) again. In some embodiments, a user need not disable/disengage the hand controller at this time. Regardless, under the "Teach" box on the "Mode Controls" tab, a user can select (e.g., highlight by touching the screen) the "Start Point" entry and select the "Set Point" button to send a command to the computer system defining the starting location for the automated movement (see FIG. 13). The dataset that the computer systems receives as a result of this command (e.g., input, and the same is true for one set of embodiments of every point/location that may be used in the definition process) may comprise data sufficient for the computer system to determine the (a) location in terms of X, Y and Z Cartesian coordinates of the tool tip in any suitable coordinate system (such as the coordinate system of the robotic arm, which may be mapped to image space (e.g., magnetic resonance imaging space) for the purpose of creating the virtual tool overlay shown in some of the figures (e.g., magnetic resonance imaging space), and (b) the orientation of the longitudinal axis of the tool (see FIG. 12 for a depiction of a such an axis). Data accessible to the computer system, such as robotic arm link lengths, may be used in the determination.

For each desired intermediary waypoint of the automated movement being programmed, the hand controller, if disabled/disengaged, may be enabled as described above and used to move the virtual manipulator to any desired location. When a desired location is reached, a user can, if he chooses, disable the hand controller as described above, and then under the "Teach" box on the "Mode Controls" tab select "Add" to create the waypoint, followed by selecting the "Set Point" button to send a command to the computer system defining the location of the desired waypoint in the automated movement. This can be repeated for each desired waypoint in the automated movement. The computer system may be configured such that after each waypoint is defined, a line on the screen is drawn between the new point and the previously defined point describing the programmed path (see FIG. 14).

A user can define the end or destination location for the automated movement in similar fashion. For example, the user may ensure that the hand controller is enabled, move the virtual manipulator to the desired location for the destination point, disable the hand controller if desired, and under the "Teach" box on the "Mode Controls" tab select (e.g., highlight by touching the screen) the "Destination Point" entry and select the "Set Point" button to send a command to the computer system defining the destination point for the automated movement. The computer system may be configured to cause the CSD screen to then show one or more line segments between the starting point, through each of the defined waypoints (if any), and to the destination point (see FIGS. 14 and 15).

Automated Movement Verification

Figure 15:
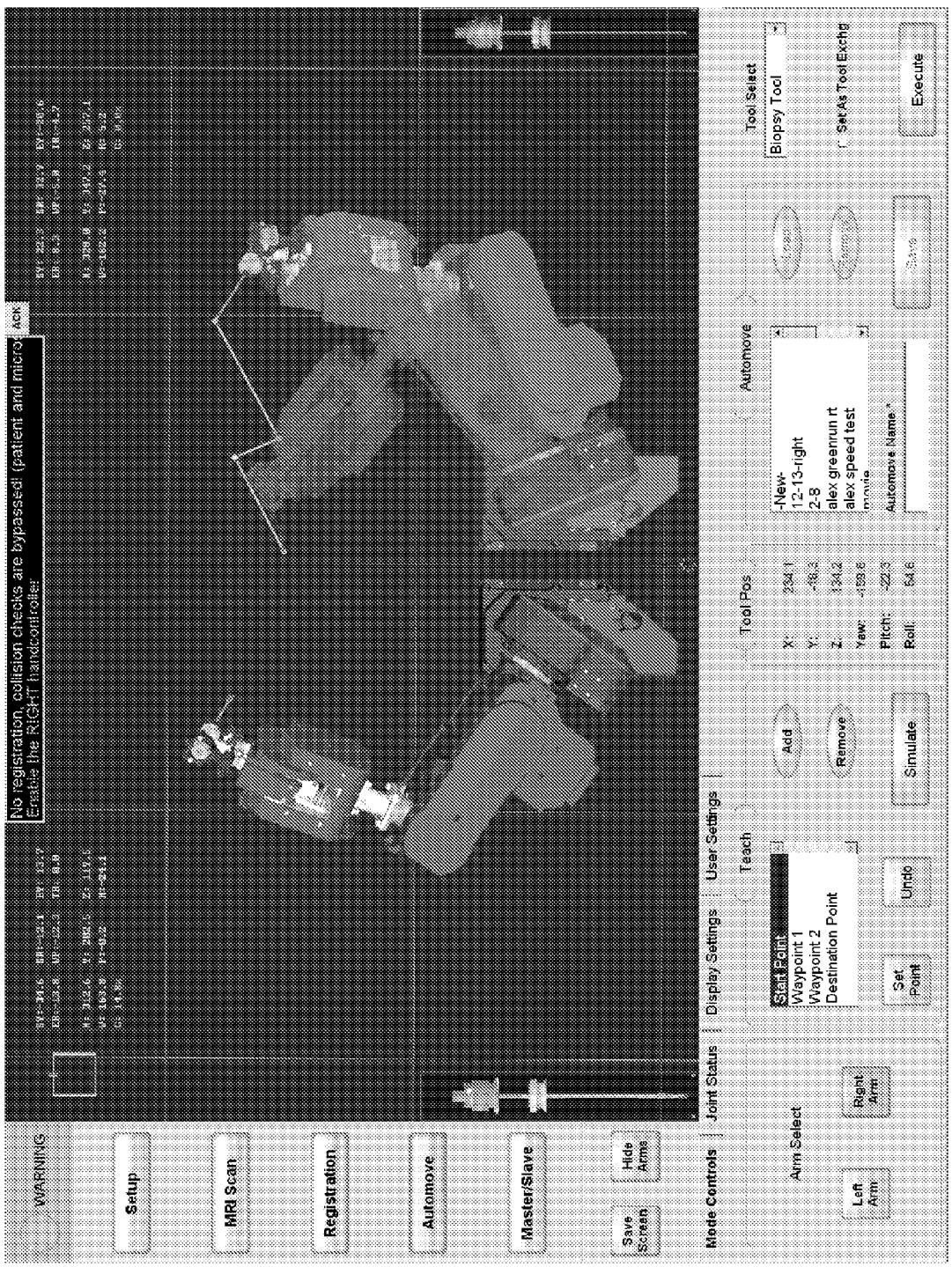
FIG. 15 shows the result of pushing the "Simulate" button such that the graphical representation of the right arm follows the path defined by the four depicted points. In this mode, the moving right arm is highlighted as it moves from the Start Point to the Destination Point and overlays an unhighlighted version of the right arm that illustrates the location of the real manipulator.
Figure 16:
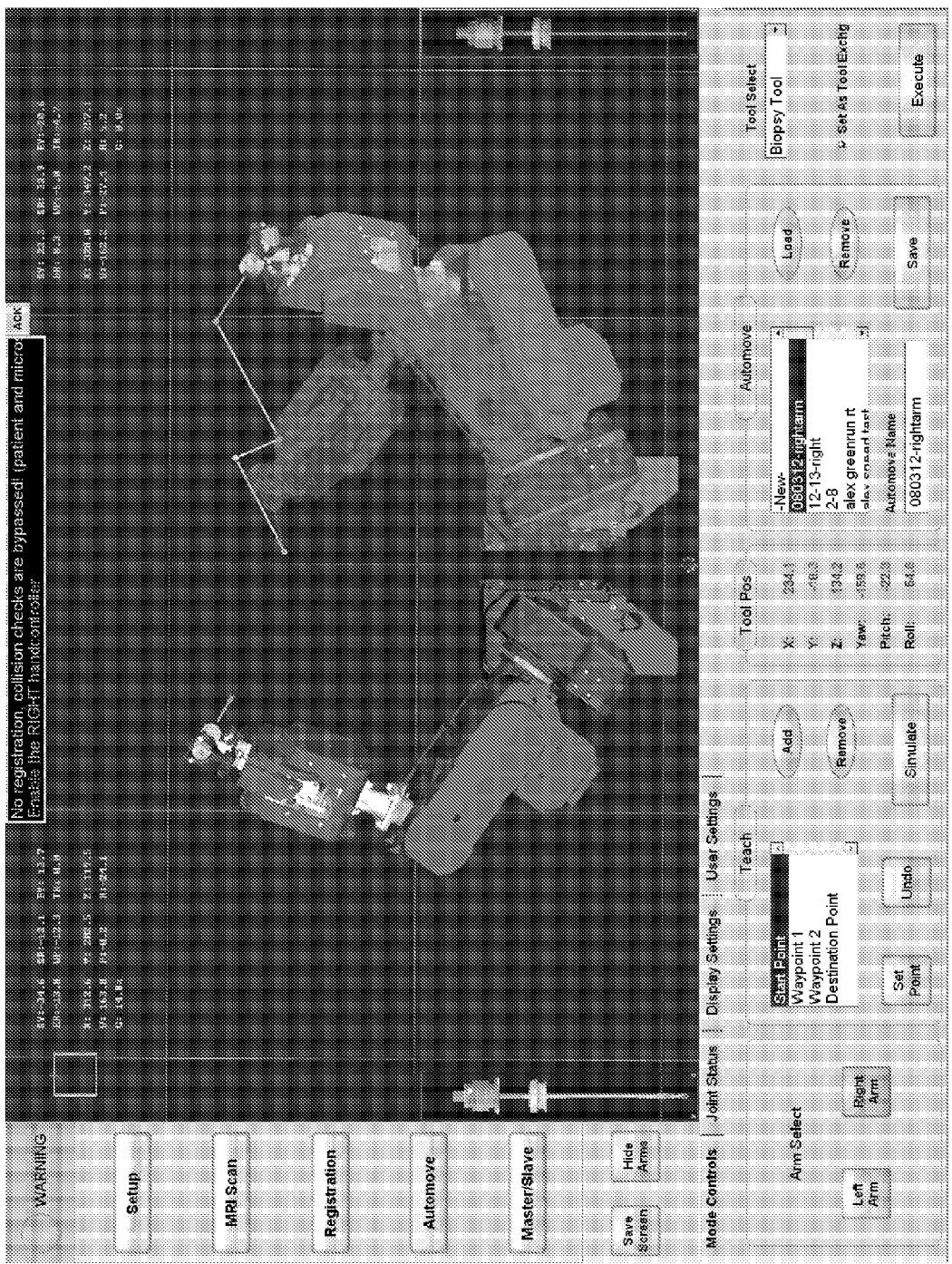
FIG. 16 shows the result of a user naming the automove illustrated in FIGS. 14 and 15 and saving it to memory by pushing the "Save" button.

The computer system may be configured such that, after the automated movement has been defined as described above, the automated movement may be simulated to allow the operator to verify that the motion as programmed is as intended. To make such a verification, the virtual manipulator as shown on the GUI should be within a valid range (e.g., it should satisfy one of the present proximity conditions) of the start or end point of the selected automated movement. A user may press the "Simulate" button in the "Teach" box of the "Mode Controls" tab (see FIG. 15), which will cause the virtual manipulator to move from one end of the automated movement to the other. As shown in FIG. 15, the computer system may be configured to show a highlighted version of the virtual manipulator move overlaying an unhighlighted version of the manipulator that remains in the pose of the real manipulator.

The computer system may be configured to detect collisions in this simulation mode. Further, it may be configured to display a suitable error message if a collision or collisions are detected that would be caused by execution of the automated movement, or if movement through any sections along the path would exceed a robotic arm joint limit or velocity limit. The computer system may be configured such that an entire automated movement may not be valid even though the virtual manipulator can reach the start and end points because the actual manipulator may have to pass through an area that it cannot physically reach. In such an instance, the automated movement may be edited as described below, and a simulation of the same run again.

Associating A Selected Robotic Arm with a Stored Automated Movement

The computer system may be configured such that a user may program (and store) any number of automated movements, but only one of the automated movements can be selected for execution (e.g., as a tool exchange automated movement) by a given manipulator. To associate an automated movement with a robotic arm for execution, in the Automove page, just above the "Execute" button on the "Mode Controls" tab is the checkbox entitled "Set As Tool Exchg." For the automated movement that a user wishes to specify as the tool exchange automated movement for a given robotic arm, the user can highlight the name of that automated movement in the list under the "Automove" box, press the "Load" button, and then check the "Set As Tool Exchg" box. See FIG. 16.

Saving, Loading, and Editing Automated Movements

The computer system may be configured to save multiple automated movements independently for the left and right robotic arms.

The computer system may be configured such that, to save an automated movement after it is defined (and after it is verified, if verification is performed), a user may select the text entry field under "Automove Name" in the "Automove" box of the "Mode Controls" tab, causing an onscreen keyboard to appear (not shown). A user may type a name for the automated movement just defined, and then press the "OK" button that appears with the keyboard. Next, the user may hit the "Save" button on the GUI in the "Automove" box of the "Mode Controls" tab (see FIG. 16). The computer system may be configured to provide a status message (see the box at the top of FIGS. 13-16 next to the ACK button) that indicates whether the automated movement was saved without errors.

The computer system may be configured such that an automated movement may be loaded by a user after it is saved. For example, a list box contains all of the previously defined automated movements for the selected robotic arm under the "Automove" box of the "Mode Controls" tab in the "Automove" settings page. A user can highlight the automated movement he wishes to load and then press the "Load" button. If the user wishes to use this loaded automated movement as the tool exchange motion for the selected robotic arm, he can do so by following the steps described above. If the user wishes to edit or replace the loaded automated movement, he may remove a point or points (up to all of them, allowing the user to start over) in the automated movement by highlighting the relevant point in the list of points shown in the "Teach" box and then pressing "Remove," and add a point or points to the automated movement using, for example, the technique discussed above. When edits are complete, and any desired verification step performed, a user can save the edits by pushing the "Save" button in the "Automove" box. See FIG. 16. The computer system may be configured to ask the user to confirm, through a pop-up box, that the "Save" button be pressed a second time to confirm the overwrite. The computer system may be configured such that the user can then check the status message to ensure that the edited/new automated movement was saved without errors.

A user may delete a saved automated movement by clicking the "Remove" button instead of the "Load" button after highlighting the name of the automated movement in the list box. See FIG. 16.

Executing an Automated Movement

The present computer systems may be configured to execute automated movements in multiple ways. For example, a command may be sent from either the GUI or from a hand controller.

From the GUI:

From the Automove page of the CSD GUI, as shown for example in FIGS. 12-16, a user may: select a robotic arm (as described above), load a saved automated movement (as described above) or have finished the creation of an automated movement (as described above), ensure that the robotic arm is powered (as described above) and associated with the automated movement that was loaded or just created, ensure that the associated robotic arm is near the start or end point of the automated movement, and select (e.g., press) the "Execute" button in the bottom right-hand part of the GUI on the "Mode Controls" tab. As a result, the robotic arm executes the loaded/finished automated movement. Further, the computer system may be configured such that pressing the "Execute" button again reverses the previously executed automated movement. In a preferred embodiment, the computer system may be configured to require that the enable button on the hand controller be depressed and held after the "Execute" button is pressed, thus better ensuring that an operator is holding the hand controller if actual manipulator movement is occurring. In such embodiments, the computer system may be configured such that depressing the enable button again will cause the motion to stop, and a subsequent depression and hold will cause the motion to reverse.

From the Input Device:

A user may load an automated movement (as described above) and specify it as the tool exchange motion (as described above); designate microsurgery mode (as described above); enter a master-slave mode by selected (e.g., pressing) the "Master/Slave" button at the left of the GUI (see, e.g., FIG. 17); using the relevant input device, move the robotic arm to a location near the start or end point of the tool exchange automated movement; and apply a sharp click followed by a sustained (e.g., two second) hold of the button on the input device (e.g., button 16 on stylus 12 of input device 10), where the computer system is configured to recognize the extended hold as a command that the operator wishes to perform a tool exchange. The automated movement specified as the tool exchange motion will be executed, provided any relevant proximity condition is satisfied. In that regard, a proximity condition may involve a check of whether the tip (e.g., the distal tip) of a tool held by the manipulator is either sufficiently close to the start point or to the end point of the automated movement. The computer system may be configured such that, if not, a sphere for each programmed zone will be shown on the CSD GUI, thus identifying the acceptable boundaries. See FIG. 18. A user can then use the CSD GUI to move the robotic arm such that the tool tip is within a boundary and restart the automated movement in the manner described above.

The computer system may be configured such that releasing the stylus enable button before the automated movement begins causes the automated movement not to execute. Otherwise, when the automated movement begins, the user can release the enable button, and motion will continue through the path to the destination point. The computer system may be configured such that the automated movement may be reversed once it has completed in the forward direction by a press and hold of the enable button on the input device in the same manner that started the automated movement. One the reverse automated movement starts, the button may be released and the motion will start and continue until the reverse path has completed. The computer system also may be configured to allow a user to interrupt an automated movement at any time during its execution by briefly pressing the hand controller enable button. A quick press of the same button will cause the robotic arm to stop. Another click and hold will move the tool back to the start point for the movement, and during that return if the user desires to continue with the original movement, he may press the enable button yet again to cause the robotic arm to stop. Another click and hold will cause arm to re-continue the original, interrupted motion.

A tool exchange nurse may decouple the robotic arm from its current tool at the tool exchange location (e.g., the destination point for the automated movement), couple a new tool to the robotic arm, and scan the new tool using a data matrix reader either while the robotic arm is stationary or in motion. The computer system may also be configured to support scanning two tools held in the two arms.

Execution Speed for Automated Movements

The computer system may be configured to provide, as in the disclosed embodiment, three speeds at which an automated movement can be executed: slow, medium and fast. The computer system may also be configured, as in the disclosed embodiment, such that the chosen speed applies to each automated movement subsequently selected for execution until a speed change selection is made.

Figure 17:
FIG. 17 shows the CSD GUI following a user's selection of "Master/Slave" mode, with the arms being out of Automove mode (which corresponds to a programming mode), and also showing that the user has selected the radio button for causing the chosen automated movement to be "Fast" in speed.
Figure 18:
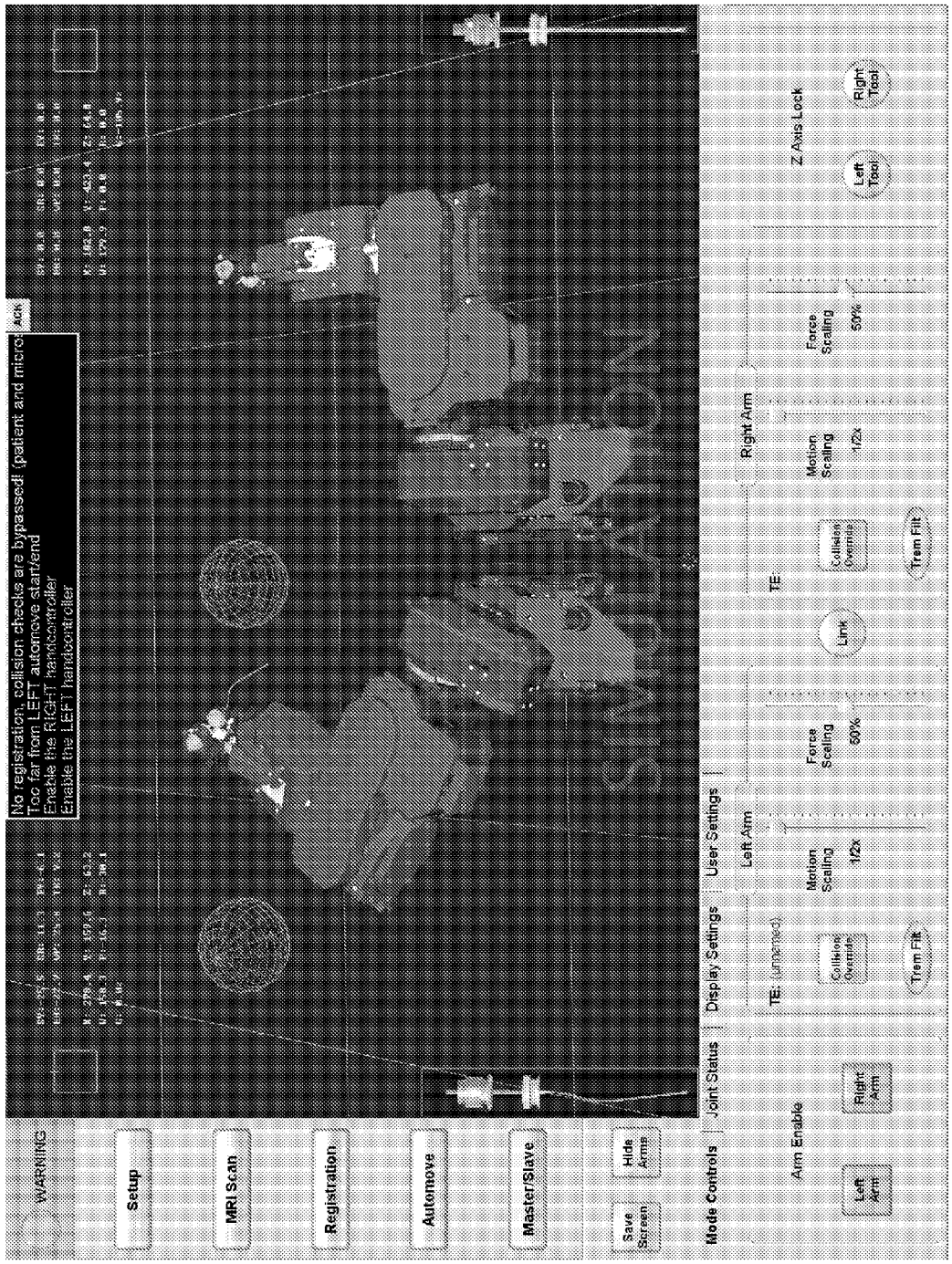
FIG. 18 shows the CSD GUI following a user's failed attempt to execute an automove because an applicable proximity condition was not satisfied.

In order to select a speed, a user may select the "User Settings" tab of the Automove page, as shown in FIG. 17. The user may select the desired speed ("Fast," "Med," or "Slow") using the radio buttons beneath the "Options" box of this tab.

Setup Considerations

Prior to creating an automated movement for use with a given subject (e.g., a patient), via training/simulation or otherwise, one or both robotic arms may be registered with one or more two-dimensional images (e.g., the 2D images of a 3D dataset of images taken with a 3D imaging modality, such as a magnetic resonance imaging (MRI) machine) of the subject (e.g., a patient). However, automated movements may be created and executed without performing such registration, though safety checks such as collision with no-go zones (defining, for example, the patient's head boundary or structures near the operating site, such as the microscope, the bore of the MRI machine, cameras, etc.) cannot otherwise be performed. A suitable technique for accomplishing such registration through a process that involves both physical registration and registration involving image space is disclosed in co-pending International Application No. PCT/US08/60538, which is incorporated by reference.

Software Algorithms

In some embodiments of the present devices and computer systems, software can be written for achieving the functions described above, and may comprise three pieces: 3D visualization, path generation, and path execution.

3D Visualization

Visualization of a given virtual robotic arm on a suitable GUI (see, e.g., FIGS. 11-18) during the automated movement creation/definition phase can be based on the use of virtual reality modeling language (VRML) models based on engineering computer-aided design (CAD) models of the robotic arm mechanical components, rendered with OpenGL® graphics. The VRML models can be compiled into OpenGL call lists and positioned in 3D space using robot kinematics calculations. The kinematics routines provide the position and orientation (x, y, z, pitch, yaw, roll) of each robotic arm segment given either the arm joint angles or end-effector pose.

Path Generation

In some embodiments, a given automated movement may comprise a list of two or more user-defined points, each describing a complete Cartesian tool pose (x, y, z, pitch, roll, yaw). These points form the basis for generating an automated movement path, which can interpolate intermediate points along straight-line segments between each pair of user-defined points. The intermediate path points (which are those that are not specifically defined by a user) can be spaced at intervals that correspond to ten milliseconds of motion and may be represented in joint space. Thus, each point along the path (both user-defined and interpolated) may comprise a set of six joint angles (Shoulder Yaw, Shoulder Roll, Elbow Yaw, Elbow Roll, Wrist Pitch, Tool Roll) when the automated movement is to be executed and was set up using a six-degree of freedom robotic arm, such as those shown in the figures and disclosed in the '316 patent. There can be hundreds of interpolated path points between each pair of user-defined Cartesian path points.

During path calculation each set of joint angles along the path can be obtained from a linearly interpolated Cartesian pose through inverse kinematics. The inverse kinematics can use an approach where closed-form absolute kinematic equations yield five of six resulting joint angles while the sixth (tool roll) is obtained through a one-dimensional numerical minimization process (a type of algorithm to minimize the result of a function y=f(x), which is well known to those of ordinary skill in the art) that uses a combination of golden section search and successive parabolic interpolation. Accuracy would be poor without taking into account robotic calibration parameters measured from the as-built robotic arm parts, which can be applied using the kinematic Jacobian matrix (a well known algorithm to those of ordinary skill in the art) in an iterative refinement loop until desired accuracy is achieved.

Each point along the calculated path can be checked for collisions against known obstacles (microscope, patient head region, surgical table) and the other arm (if present). The collision checks, which can be performed at a frequency of 100 Hz per robotic arm during operation but even more frequently during calculation of an automated movement path, can be based on the use of any suitable collision detection algorithm available to those of ordinary skill in the art, such as VCollide, an efficient polygon interference algorithm designed to operate on large numbers of polygonal objects. Vcollide makes no assumptions about input structure and works on arbitrary models, also known as "polygon soups." Vcollide uses a three-stage collision detection architecture characterized by an N-body test that finds possibly colliding pairs of objects, a hierarchical oriented bounding box test that finds possibly colliding pairs of triangles, and an exact test that determines whether or not a pair of triangles actually overlaps.

As those of ordinary skill in the art will understand, the closed-form absolute kinematic equations can be used where sufficient details of the physical structure of the robotic arm—e.g., dimensions, effective link lengths between joints, and the like—are known and permit a closed form solution to exist. In the case of the arms disclosed in the figures and the '316 patent, the closed-form absolute kinematic equations can be used when the wrist yaw joint (seventh joint) of the robotic arm is removed, such as to provide a closed form solution.

Path Execution

Execution of an automated movement involves commanding the robot hardware to move to each successive point along the automated movement path at ten millisecond (ms) intervals. Because the path is represented in joint space there is no need to re-calculate inverse kinematics. During execution, collision checks may be repeated for safety in case the position of scene objects has changed or the robotic arm does not exactly follow the commanded path. To achieve smooth motion, the point one ahead of the intended target point is the one actually commanded to the joint motion controller, with a commanded time interval of twenty ms. After ten ms have elapsed, the destination is altered with a new destination point which is again twenty ms ahead.

Embodiments of the present techniques may be coded as software stored on any suitable computer readable media (e.g., tangible computer readable media) to form the present devices, such as any suitable form of memory or data storage device, including but not limited to hard drive media, optical media, RAM, SRAM, DRAM, SDRAM, ROM, EPROM, EEPROM, tape media, cartridge media, flash memory, memory stick, and/or the like. Tangible computer readable media includes any physical medium that can store or transfer information. Such embodiments may be characterized as tangible computer readable media having (or encoded with) computer executable (e.g., machine readable) instructions for performing certain step(s). The term "tangible computer readable medium" does not include wireless transmission media, such as carrier waves. The term "computer readable medium," however, does cover wireless transmission media, and some embodiments of the present methods may include wireless transmission media carrying the computer readable instructions described above. The software can be written according to any technique known in the art. For instance, the software may be written in any one or more computer languages (e.g., ASSEMBLY, PASCAL, FORTRAN, BASIC, C, C++, C#, JAVA, Perl, Python) or using scientific packages like, but not limited to, Matlab®, R, S-plus®, and SAS®. The code may be to enable it to be compiled on all common platforms (e.g., Microsoft®, Linux®, Apple Macintosh® OS X, Unix®). Further, well-established cross-platform libraries such as OpenGL® may be utilized to execute embodiments of the present methods, devices and systems. Multi-threading may be used wherever applicable to reduce computing time on modern single- and multi-processor based hardware platforms. As discussed above and illustrated in the figures, the software may include a GUI, which may provide a user with a more intuitive feel when running the software. Different fields may be accessible by screen touching, a mouse and/or keyboard. Alarms, cues, and the like may be done via pop-up windows, audible alerts, or any other techniques known in the art.

Some (up to all) of the functions described above may be implemented using a computer having a processor (e.g., one or more integrated circuits) programmed with firmware and/or running software. Some (up to all) of the functions described above may be implemented using a distributed computing environment, which is one example of a computer system. In a distributed computing environment, multiple computers may be used, such as those connected by any suitable number of connection mediums (e.g., a local area network (LAN), a wide area network (WAN), or other computer networks, including but not limited to Ethernets, enterprise-wide computer networks, intranets and the Internet, and the connections between computers can be wired or wireless). Servers and user terminals can be part of a given computer system. Furthermore, embodiments of suitable computer systems may be implemented on application specific integrated circuits (ASICs) or very large scale integrated (VLSI) circuits, and further (or alternatively) may be configured to use virtualization of resources, virtual computing, and/or cloud computing to achieve the specified functions. In fact, persons of ordinary skill in the art may utilize any number of suitable structures capable of executing logical operations in order to achieve the functions described above in a computer system consistent with this disclosure.

Descriptions of well known processing techniques, components and equipment have been omitted so as not to unnecessarily obscure the present methods, devices and systems in unnecessary detail. The descriptions of the present methods, devices and systems are exemplary and non-limiting. Certain substitutions, modifications, additions and/or rearrangements falling within the scope of the claims, but not explicitly listed in this disclosure, may become apparent to those of ordinary skill in the art based on this disclosure. For example, while the "Automated Movement Creation" section above explains how points of a given automated movement may be created using a GUI, other embodiments of the present techniques (in the form of, for example, computer readable media, computer systems, or a method (such as one that is computer-implemented)) may be configured to enable identification of a given point in an automated movement to be defined when a user manipulates a hand controller linked to the relevant robotic arm, such as by depressing lever 14. Furthermore, it will be appreciated that in the development of a working embodiment, numerous implementation-specific decisions must be made to achieve the developers' specific goals, such as compliance with system-related and business-related constraints, which will vary from one implementation to another. While such a development effort might be complex and time-consuming, it would nonetheless be a routine undertaking for those of ordinary skill in the art having the benefit of this disclosure.

The appended claims are not to be interpreted as including means-plus-function limitations, unless such a limitation is explicitly recited in a given claim using the phrase(s) "means for" and/or "step for," respectively.

The invention claimed is:

1. A computer-implemented method for automated movement of a robotic arm of a surgical robot, the robotic arm configured for movement under an automove mode and under a master-slave mode, the method comprising at least the following steps:
   a. receiving a designation of at least one automated robotic arm movement, the automated robotic arm movement comprising a programmed starting position for a tool operatively associated with the robotic arm, and a programmed termination position for the tool;
   b. receiving coordinates of a position of the tool;
   c. receiving an instruction to execute the automated robotic arm movement; and either
   d. executing the automated robotic arm movement if a proximity condition is satisfied, the proximity condition relating to the position of the tool relative to the programmed starting position, wherein execution of the automated robotic arm movement causes the tool to move to the programmed termination position, or
   e. if the proximity condition is not satisfied, generating an output indicative of the position of the tool relative to the programmed starting position, thereby enabling user-guided movement of the robotic arm under the master-slave mode such that the proximity condition is satisfied.

2. The method of claim 1, wherein the programmed starting position is defined relative to a tip of the tool, and the proximity condition relates to the position of the tip of the tool relative to the programmed starting position.

3. The method of claim 1, wherein actuation of a button or a lever on a master hand controller generates the instruction in step c.

4. The method of claim 1, further comprising at least the following steps:
   e. receiving an instruction to execute a second automated robotic arm movement that comprises movement by the robotic arm away from the programmed termination position; and
   f. executing the second automated robotic arm movement if a second proximity condition is satisfied, the second proximity condition relating to the position of the tool relative to the programmed termination position, wherein execution of the automated movement causes the tool to move away from the programmed termination position.

5. The method of claim 1, further comprising at least the following steps:
   receiving an instruction to interrupt the automated robotic arm movement; and
   stopping the automated robotic arm movement.

6. The method of claim 1, wherein the programmed termination position corresponds to a tool exchange location.

7. The method of claim 1, wherein
   step a. comprises receiving designations of multiple automated robotic arm movements, each automated robotic arm movement comprising at least a programmed starting position for the tool and a programmed termination position for the tool; and
   step c. comprises receiving an instruction to execute one of the multiple automated robotic arm movements.

8. The method of claim 7, wherein the method is for automated movement of a robotic arm of a surgical robot having two or more robotic arms, each robotic arm configured for movement under an automove mode and under a master-slave mode, and wherein the method further comprises:
   receiving a command selecting one of the robotic arms for execution of the automated robotic arm movement.

9. The method of claim 7, further comprising the steps of:
   displaying a graphical user interface having one or more data entry elements that enable at least the following:
      i. definition of each of the multiple automated robotic arm movements by defining at least the starting position and the termination position for each automated robotic arm movement, and
      ii. selection of a robotic arm of the surgical robot to execute one or more of the multiple automated robotic arm movements.

10. The method of claim 9, wherein the one or more data entry elements of the graphical user interface further enable at least the following:
    selection of a simulation mode in which to define the multiple automated robotic arm movements;
    and wherein the method further comprises at least the following steps:
       displaying a graphical representation of the robotic arm on the graphical user interface, and
       moving the graphical representation in response to movement of an input device without also causing actual movement of the robotic arm.

11. The method of claim 9, wherein the one or more data entry elements of the graphical user interface further enable at least the following:
    selection of the tool to be operatively associated with the selected robotic arm.

12. The method of claim 9, further comprising at least the following steps:
    displaying a graphical representation of one or two robotic arms of the surgical robot on the graphical user interface;
    receiving a command from an input device associated with a given robotic arm; and
    moving the graphical representation of that robotic arm on the graphical user interface in response to manipulation of the input device, such that the graphical user interface displays the effect of the manipulation of the input device on movement of that robotic arm.

13. The method of claim 12, further comprising at least the following step:
    displaying a graphical representation of a head of a subject on the graphical user interface.

14. The method of claim 12, further comprising at least the following steps:
    receiving a disable command from the input device associated with a given robotic arm; and
    decoupling manipulation of the input device and movement of the graphical representation of that robotic arm on the graphical user interface.

15. The method of claim 9, further comprising at least the following step:
    displaying a path defined by the programmed starting position and the programmed termination position of the automated robotic arm movement on the graphical user interface.

16. The method of claim 15, wherein the one or more data entry elements of the graphical user interface further enable at least the following:

definition of one or more intermediate positions between the programmed starting position and the programmed termination position of an automated robotic arm movement;

and wherein the method further comprises at least the following step:

displaying a path defined by the programmed starting position, the one or more intermediate positions and the programmed termination position of the automated robotic arm movement.

17. The method of claim 1, further comprising defining the programmed starting position and the programmed termination position by designating a first dataset for the programmed starting position and designating a second dataset for the programmed termination position.

18. The method of claim 17, wherein the tool operatively associated with the robotic arm has a longitudinal axis and the first dataset and second dataset include data sufficient to enable the determination of a position of a tip of the tool and the orientation of the longitudinal axis of the tool.

19. The method of claim 18, wherein execution of the automated robotic arm movement comprises movement of the tool along an axis that is not coincident with the longitudinal axis of the tool.

20. The method of claim 1, further comprising at least the following steps:

receiving a command to execute a reverse of the automated movement after the execution of the automated movement is complete; and executing the reverse of the automated movement such that the robotic arm moves away from the termination position towards the starting position.

21. The method of claim 1, wherein the proximity condition is satisfied when the tool is within a predefined region, the predefined region surrounding the programmed starting point.

22. The method of claim 21, wherein the predefined region corresponds to a location external to a patient's body.

23. The method according to claim 1, wherein the automated robotic arm movement further comprises one or more programmed waypoints between the programmed starting position and the programmed termination position.

24. A computer readable medium having stored thereon machine readable instructions for performing at least the steps recited in claim 1.

25. A computer system configured to control movement of a robotic arm of a surgical robot, the robotic arm configured for movement under an automove mode and under a master-slave mode, the system comprising:

a computing device operatively associated with the surgical robot and configured to implement the method for automated movement of a robotic arm according to claim 1, one or more input devices operatively associated with the computing device for inputting commands relating to at least the automated robotic arm movement, and a graphical user interface operatively associated with the computing device for displaying at least a graphical representation of the robotic arm and data relating to the automated robotic arm movement.

* * * * *